(12) United States Patent
Branch et al.

(10) Patent No.: US 10,842,439 B2
(45) Date of Patent: Nov. 24, 2020

(54) BIOMECHANICAL CHARACTERIZATION AND ANALYSIS OF JOINTS

(71) Applicant: ERMI, Inc., Atlanta, GA (US)

(72) Inventors: Thomas P. Branch, Atlanta, GA (US); Shaun K. Stinton, Chamblee, GA (US); Edward Dittmar, Marietta, GA (US); Nathaniel K. deJarnette, Lilburn, GA (US); T. Christopher Madden, Atlanta, GA (US)

(73) Assignee: RoboDiagnostics LLC, Atlanta, GA (US)

( * ) Notice: Subject to any disclaimer, the term of this patent is extended or adjusted under 35 U.S.C. 154(b) by 470 days.

(21) Appl. No.: 15/173,199

(22) Filed: Jun. 3, 2016

(65) Prior Publication Data

US 2017/0347962 A1     Dec. 7, 2017

(51) Int. Cl.
*A61B 5/00*    (2006.01)
*A61B 34/30*   (2016.01)
(Continued)

(52) U.S. Cl.
CPC ............ *A61B 5/702* (2013.01); *A61B 5/1121* (2013.01); *A61B 5/4585* (2013.01); *A61B 34/30* (2016.02);
(Continued)

(58) Field of Classification Search
CPC ............ A61B 2034/105; A61B 5/4528; A61B 5/1121; A61B 2562/0219; A61B 2562/0252; A61B 5/107; A61B 5/112; A61B 17/025; A61B 17/1642; A61B 17/1671; A61B 17/3472; A61B 17/1675;
(Continued)

(56) References Cited

U.S. PATENT DOCUMENTS

| 4,969,471 A | 11/1990 | Daniel et al. |
| 5,935,086 A | 8/1999 | Beacon et al. |

(Continued)

FOREIGN PATENT DOCUMENTS

| WO | 2014076147 A2 | 5/2014 |
| WO | 2015121830 A1 | 8/2015 |

OTHER PUBLICATIONS

MTS Systems Corporation. MTS TestSuite™ TW Elite User Guide (2015): 1-684.*

(Continued)

*Primary Examiner* — May A Abouelela

(74) *Attorney, Agent, or Firm* — Lempia Summerfield Katz LLC

(57) ABSTRACT

A method includes obtaining load-deformation data for a joint, the load-deformation data being gathered via joint testing implemented by robotic test equipment, the robotic test equipment being configured for movement of the joint and comprising sensors to gather the load-deformation data during the movement. A load-deformation curve function for the load-deformation data is generated, the load-deformation curve function defining a curve fitted to the load-deformation data. A feature of the curve defined by the load-deformation curve function is quantified. A biomechanical characteristic of the joint is identified based on the quantified feature of the curve defined by the load-deformation curve function.

23 Claims, 11 Drawing Sheets

(51) Int. Cl.
*A61B 5/11* (2006.01)
*A61B 34/10* (2016.01)
*A61B 34/20* (2016.01)

(52) U.S. Cl.
CPC ............ *A61B 5/7246* (2013.01); *A61B 34/20* (2016.02); *A61B 2034/105* (2016.02); *A61B 2562/0252* (2013.01)

(58) Field of Classification Search
CPC . A61B 17/8805; A61B 1/0016; A61B 1/0057; A61B 5/4504; A61B 2002/4667; A61B 2002/4668; A61F 2002/4667; A61F 2002/4668
USPC ......... 600/300, 587, 595; 606/90; 623/20.34
See application file for complete search history.

(56) References Cited

U.S. PATENT DOCUMENTS

| | | | |
|---|---|---|---|
| 6,162,189 | A | 12/2000 | Girone et al. |
| 6,324,296 | B1 | 11/2001 | McSheery et al. |
| 7,291,119 | B1 | 11/2007 | de Guise et al. |
| 7,607,440 | B2 | 10/2009 | Coste-Maniere et al. |
| 8,170,716 | B2 | 5/2012 | Coste-Maniere et al. |
| 8,317,730 | B2 * | 11/2012 | Zhang ................. A61F 5/0102 600/587 |
| 8,491,574 | B2 | 7/2013 | Blumenkranz |
| 8,571,710 | B2 | 10/2013 | Coste-Maniere et al. |
| 8,888,718 | B2 | 11/2014 | Siston et al. |
| 2003/0109780 | A1 | 6/2003 | Coste-Maniere et al. |
| 2005/0119661 | A1 | 6/2005 | Hodgson et al. |
| 2005/0234332 | A1 | 10/2005 | Murphy |
| 2005/0288609 | A1* | 12/2005 | Warner ................. A61B 5/103 600/592 |
| 2006/0161051 | A1 | 7/2006 | Terrill-Grisoni et al. |
| 2007/0055176 | A1 | 3/2007 | Branch et al. |
| 2009/0124936 | A1 | 5/2009 | Branch et al. |
| 2010/0010506 | A1 | 1/2010 | Murphy |
| 2012/0046540 | A1* | 2/2012 | Branch ................ A61B 5/1036 600/415 |
| 2013/0041289 | A1 | 2/2013 | Sena et al. |
| 2013/0282024 | A1 | 10/2013 | Blumenkranz |
| 2013/0307955 | A1 | 11/2013 | Deitz et al. |
| 2014/0081181 | A1 | 3/2014 | Branch et al. |
| 2014/0135985 | A1 | 5/2014 | Coste-Maniere et al. |
| 2014/0222157 | A1 | 8/2014 | Al Hares et al. |
| 2014/0316242 | A1 | 10/2014 | Musahl et al. |
| 2015/0201867 | A1 | 7/2015 | Peindl et al. |

OTHER PUBLICATIONS

MTS Systems Corporation. MTS Bionix® Tabletop Test Systems (2013): 1-12.*
Woo, Savio LY, et al. "Biomechanics of knee ligaments." The American journal of sports medicine 27.4 (1999): 533-543.*
Andrew J. Harrison, "Applications of Functional Data Analysis in Sport Biomechanics", 32 International Conference of Biomechanics in Sports, Sep. 30, 2014, 9 pages, Biomechanics Research Unit, University of Limerick, Ireland.
Elizabeth Crane et al., "Functional Data Analysis for Biomechanics", Theoretical Biomechanics, Nov. 2011, pp. 77-92.

* cited by examiner

BIOMECHANICAL CHARACTERIZATION AND ANALYSIS OF JOINTS

CROSS-REFERENCES TO RELATED APPLICATIONS

This application is related to the concurrently filed and commonly assigned applications entitled "Joint Play Quantification and Analysis" (U.S. patent application Ser. No. 15/173,157), "Robotic Joint Testing Apparatus and Coordinate Systems for Joint Evaluation and Testing" (U.S. patent application Ser. No. 15/173,510), "Analysis System and Method for Determining Joint Equilibrium Position" (U.S. patent application Ser. No. 15/173,520), and "Robotic Knee Testing Apparatus and Patient and Apparatus Set-Up Methods" (U.S. patent application Ser. No. 15/173,536), the entire disclosures of which are hereby expressly incorporated by reference.

BACKGROUND OF THE DISCLOSURE

Field of the Disclosure

The disclosure relates generally to robotic joint testing.

Brief Description of Related Technology

Knee injuries and ligament damage have been diagnosed using manual tests. These tests are performed by doctors or other medical personnel, i.e., clinicians, on the patient in order to detect and measure changes to joint play in order to diagnose damage to the knee ligaments or other knee joint support structures. There are a number of commonly known manual tests used to evaluate increased joint play associated with ligament injuries in the knee. The three most common tests, by their commonly used names, include the Dial test, the Lachman test, and the Varus-Valgus test. Because these tests are performed manually by individual medical personnel, these tests naturally are limited by the specific clinician's subjective evaluation. The subjective nature of the tests may hinder the precision or accuracy of any diagnosis of the extent of ligament lengthening (or damage), the change in ligament compliance or elastic resilience, i.e., stretchiness, changes in the bone structure, or combinations thereof.

The Lachman's test, or anterior-posterior drawer test at 30 degrees, is performed with a patient lying in a supine position. The clinician will bend the patient's knee joint at approximately 20 to 30 degrees. The clinician places one hand on the patient's upper thigh and their other hand below the upper part of the patient's calf. The clinician then applies upward and downward pressure under the patient's calf while opposing that force with downward and upward pressure on the patient's thigh. This induces an anterior and posterior translation between the patient's femur and tibia. The degree of translation is subjectively determined by the clinician to diagnose the injury or joint damage. In addition to the anterior and posterior motion, the clinician feels other off-primary axis motions occurring in the knee when applying the primary axis anterior-posterior load. Off-axis motions are those motions not oriented directly along the pathway of motion caused by the torque or other actuation directed to the limb. In other words, if the actuation is directed along the Y-axis in a positive and negative direction, off-axis motion would be oriented along translations along the X-axis or Z-axis, or along the rotations around all three axes.

The Dial test, or the 30 degree Tibial Axial Rotation test, is performed with the patient lying in the supine position with the knee at 30 degrees and the heel on the table. The foot is rotated in maximum internal rotation followed by maximum external rotation. The amount of rotation occurring both at the proximal tibia and at the foot is noted.

The Varus-Valgus Stress test can be performed under many conditions, the most common one having the patient supine and the lower leg cradled in the clinician's arms. Pressure is applied in abduction and adduction with movement at the foot while a hand stabilizes the femur. An assessment of both motion and separation of the joint space is noted along its medial and lateral joint line.

A fourth test combines all of the previous tests into a complex maneuver called the Pivot Shift test. The Pivot Shift test is similarly performed with the patient lying in a supine position. The leg is straightened out so that the knee joint is placed in full extension (x-axis rotation). A valgus or side-to-side outward rotation (y-axis rotation) force and an internal or twisting rotation (z-axis rotation) force is applied to the knee to allow the lateral tibia to slip anteriorly from underneath the lateral femoral condyle. As the knee is flexed or bent (x-rotation), the tibia is allowed to slip suddenly back underneath the femoral condyle. The clinician subjectively determines whether there is an abnormal external rotation (z-axis rotation) and posterior translation (y-axis translation) of the tibia with respect to the femur. The degree of shift that is felt or determined by the clinician represents to the clinician the relative increased translation (y-axis translation) of the lateral side of the knee with respect to the increased translation (y-axis translation) of the medial side of the knee. A sudden shift in the knee joint is felt by the clinician and represents the point at which the tibia bone slides from in front of the radius of curvature of the curved end of the femur back to its normal position under the femoral condyle. The Pivot Shift test is inherently subjective, difficult to accurately perform, difficult to teach, and ultimately difficult to quantify.

Grading each test usually involves the opinion of the physician placing the test into three categories, e.g., Grade I, Grade II or Grade III. For the pivot shift test, the grading depends upon the speed and intensity of the knee joint slipping back into place. For other tests, the grading represents the amount of motion detected by the clinician during the examination. For example, Grade I would be 0-5 mm of joint play. Grade II would represent 6-10 mm of joint play. Grade III would represent 11-15 mm of joint play.

For a ligament injury to be diagnosed, one or more of these tests is considered abnormal, suggesting a Grade II or more increase in joint play. In the past the results of a single test was used to diagnose a ligament tear. Often this "one dimensional" diagnosis would result in a surgical procedure. For instance, in order for a clinician to diagnose an injured ACL using the aforementioned manual tests, the clinician determines whether the knee feels abnormal. The accuracy of an ACL injury diagnosis provided by a clinician using currently known manual tests depends on the skill and experience of the clinician and their subjective determinations. A misdiagnosis can lead to unnecessary treatment or unnecessary delay in treatment, which may result in an increased risk for further injury or damage to the patient's knee joint.

A combination of these clinical examination tests can be used to diagnose lateral collateral ligament (LCL), medial collateral ligament (MCL), and posterior cruciate ligament (PCL), and other knee ligament injuries. Each manual test relies on grading the degree of length (or damage) increase in the ligament based on relative increase in joint play into three Grades or categories. There is no effort to grade the compliance or elastic resilience, i.e., stretchiness, of the ligaments using these manual tests. An expert clinician may instead describe the ligament in terms of its subjective feel to the clinician, e.g., by stating that the joint has a soft or hard endpoint. Also, a knee joint may have injury or damage to more than one ligament or structure. The more ligaments and structures of the knee joint that are damaged, the more complex it is for the clinician to perform a manual knee examination. This can make the full diagnosis less accurate and less precise.

Clinicians and surgeons manually examine the injured knee joint for altered or increased joint play. However, due to the variability in size of the patient, size and experience of the surgeon, and the potential degree or subtlety of an injury, consistent and reproducible reports of joint play between surgeons is not possible. Many reports have documented that, whether diagnosis is performed manually or even with manual arthrometers, the manual application of torque to the knee joint varies widely between clinicians. This results in inconsistencies in the examination of joint play and, ultimately, the diagnosis made by the clinician.

Others have attempted to reduce the manual nature of such joint testing by applying an instrument to the knee joint during testing. The objective has been to mechanically or objectively quantify or measure a change in the structure of the knee after ligament damage. Several devices have been developed in attempting to more accurately quantify the extent of injury or relative displacement and compliance of a ligament in the knee. In one example, such devices have been developed by Medmetric Corp. These devices include the KT-1000 and KT-2000 models. The KT devices are intended to measure the anterior-posterior translation of the tibia with respect to the femur. The KT devices attach to the patient's tibia during testing.

The KT devices attempt to quantify the findings achieved by a clinician performing the Anterior-Posterior Drawer test at 30 degrees (Lachman's test) and the Anterior-Posterior Drawer test at 90 degrees. Force is applied to a handle on the device, which measures the force and delivers the amount of applied force to the clinician, which is indicated through sounds, such as a low pitched sound for a 15 pound force and a higher pitched sound for a 20 pound force. The applied force in the KT devices pulls anteriorly along the y-axis through a strap that wraps underneath the patient's calf. The translation is determined using a technique that measures the relative motion between a pad placed against the anterior tibia and a pad placed against the patella. The KT devices do not measure relative displacement or compliance in any of the other degrees of freedom in the knee. Also, quantified results from using the KT-1000 or KT-2000 devices have been found to not correlate with patient satisfaction.

Laxity testing in the past, both manual and instrumented, has been found to be inconsistent, both when testing the same patient from day to day and when two different examiners test the same patient. This is in part due to 1) the subjective nature, among examiners and among patients, of these prior examination and diagnosis techniques, 2) the complexity of the anatomy of the knee, 3) the lack of a system or method that is reliably repeatable to measure knee laxity, and 4) the accumulation of error introduced at different stages of an examination or diagnosis. Introducing significant error at any one or more steps during a test can greatly affect, and invariably reduce, the accuracy of the ultimate diagnosis. The degree of error may often overwhelm the ability to obtain an accurate diagnosis.

SUMMARY OF THE DISCLOSURE

In accordance with one aspect of the disclosure, a method includes obtaining load-deformation data for a joint, the load-deformation data being gathered via joint testing implemented by robotic test equipment, the robotic test equipment being configured for movement of the joint and comprising sensors to gather the load-deformation data during the movement, generating a load-deformation curve function for the load-deformation data, the load-deformation curve function defining a curve fitted to the load-deformation data, quantifying a feature of the curve defined by the load-deformation curve function, and identifying a biomechanical characteristic of the joint based on the quantified feature of the curve defined by the load-deformation curve function.

In accordance with another aspect of the disclosure, a method includes obtaining load-deformation data for a joint, the load-deformation data being gathered via joint testing implemented by robotic test equipment, the robotic test equipment being configured for movement of the joint and comprising sensors to gather the load-deformation data during the movement, generating a load-deformation curve function for the joint based on the load-deformation data, generating a set of load-deformation data points for the joint using the load-deformation curve function, implementing a comparison of the set of load-deformation data points with preset load-deformation curve function data, and providing an indication of a biomechanical characteristic of the joint based on the comparison.

In accordance with yet another aspect of the disclosure, a system includes a storage device in which preset load-deformation data for a plurality of joint instances is stored, a memory in which input instructions, curve function generation instructions, and curve function analysis instructions are stored, and a processor coupled to the storage device and the memory. The processor is configured to implement the input instructions to obtain load-deformation data for a joint, the load-deformation data being gathered via joint testing implemented by robotic testing apparatus, the robotic testing apparatus being configured for movement of the joint and comprising sensors to gather the load-deformation data during the movement. The processor is configured to implement the curve function generation instructions to generate a load-deformation curve function for the load-deformation data for the joint, the load-deformation curve function defining a curve fitted to the load-deformation data. The processor is configured to implement the curve analysis instructions to quantify a feature of the curve defined by the load-deformation curve function, and to implement a comparison of the quantified feature of the curve and the preset load-deformation data to identify a biomechanical characteristic of the joint.

BRIEF DESCRIPTION OF THE DRAWING FIGURES

For a more complete understanding of the disclosure, reference is made to the following detailed description and accompanying drawing figures, in which like reference numerals may be used to identify like elements in the figures.

Figure 1:
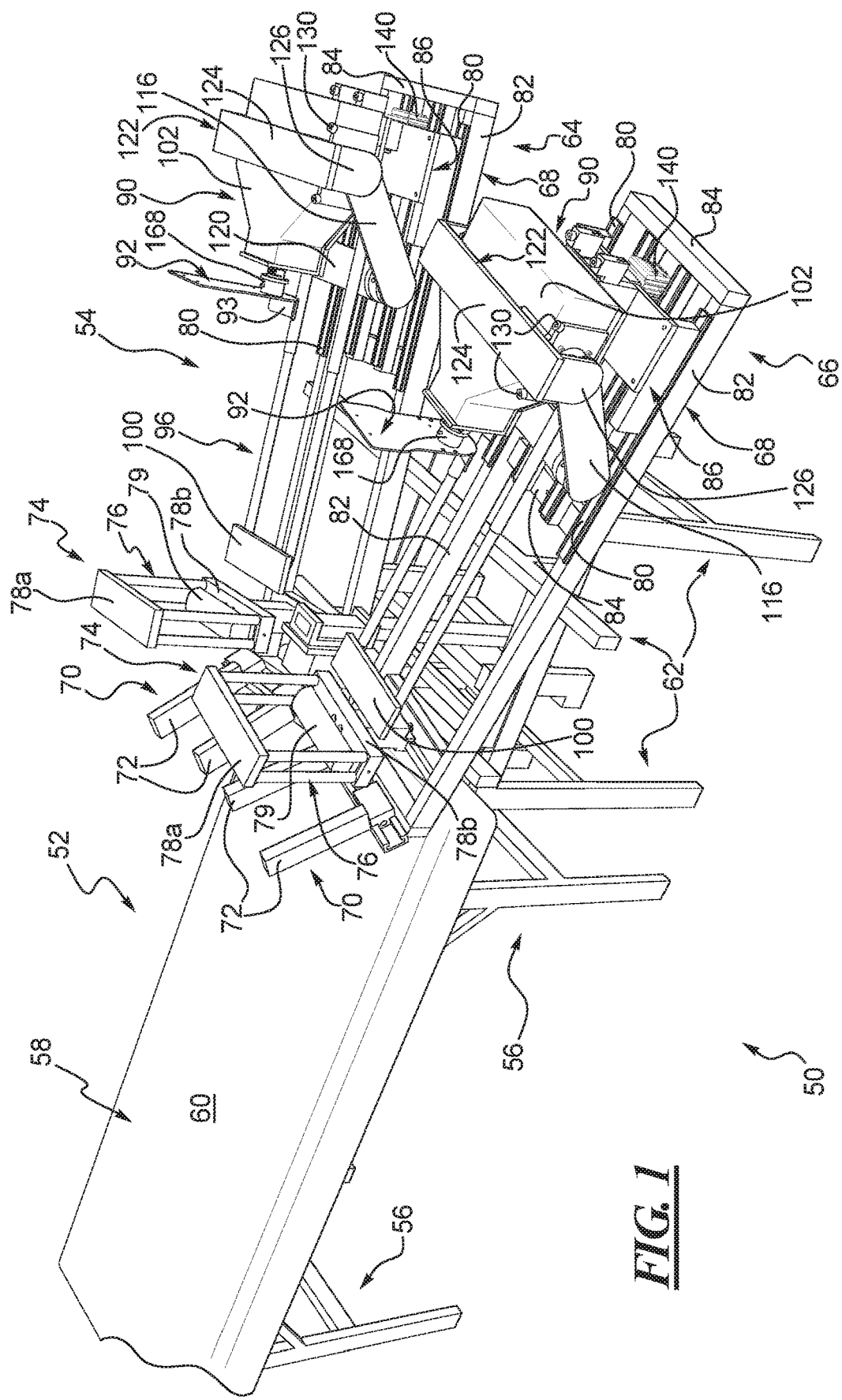
FIG. 1 shows a perspective view of one example of a robotic knee testing (RKT) apparatus according to the teachings of the present disclosure.

The disclosed methods, systems, and devices may assume various forms. Specific examples are illustrated in the drawing (and are hereafter described) with the understanding that the disclosure is intended to be illustrative, and is not intended to limit the invention to the specific examples described and illustrated herein.

DETAILED DESCRIPTION OF THE DISCLOSURE

Systems and methods for biomechanical characterization and analysis of joints are described. The characterization and analysis is based on a load-deformation curve function for load-deformation data gathered via robotic joint testing. The load-deformation curve function is fitted to the load-deformation data using one or more fitting procedures. The systems and methods may use the load-deformation curve function to characterize and evaluate the joint under test.

The generation or production of a load-deformation curve function, or load-deformation curve, may support various types of analyses (e.g., functional data analysis) of test data acquired via the robotic joint testing. The analysis may involve the use of a set of determinations applied to the test data to extract or otherwise derive information from the test data that may be indicative of whether (or not) specific injuries or other conditions are presented by the joint under test. The functional or other data analysis thus provides a technique for describing and evaluating the overall health of a joint, such as a knee. The functional or other data analysis does not simply evaluate a range of motion achieved during a particular test, such as maximum internal rotation. Instead, the functional data analysis recognizes that a joint under test can move between two endpoints in significantly different ways. The curve function of the functional data analysis addresses the movement between the endpoints for a joint under test. For instance, the particular shape of the curve defined by the curve function is meaningful. In one example, the slope of the curve at or near the endpoints (e.g., over the last 10-20% of the curve) may be indicative of the integrity of a ligament. The slope quantifies the so-called "endpoint feel", or endpoint stiffness, of the joint, thereby avoiding having to rely upon a physician's subjective assessment of endpoint feel during a manual examination. The slope may then be compared with preset data, including preset slope data, for abnormal and/or normal joints. The slope comparison may be one of multiple comparisons involving a profile of the joint under test.

Various features of the curve function may be used to characterize ligament integrity and assess other joint conditions and status. In some cases, the shape of the curve defined by the curve function may be quantified and analyzed. Curve shape may be indicative of relative joint stiffness along respective portions of the joint movement. In some cases, a pattern recognition procedure may be implemented to recognize certain curve shapes indicative of particular joint conditions. Alternatively or additionally, the curve function is used to generate data points (e.g., common torque data points) for point-wise comparisons of joints. For example, point-wise t-tests are used to compare a joint with other joints or joint groups. In these and other ways, the curve function may be used to implement statistical comparisons across the entire range of joint motion.

The fitting procedure may rely on, or target, particular portions of the load-deformation curve. One or more portions of the load-deformation data captured and provided by the robotic testing apparatus are excluded from a curve fitting procedure. For example, a curve fitting procedure may be configured such that portions of the load-deformation data at torque or load zero or other low torque or load levels are excluded, or not relied upon, for curve fitting purposes. Alternatively or additionally, a respective load-deformation curve may be fitted to each particular segment of the load-deformation data. For instance, basis spline (or b-spline) fitting procedures may be used to generate multiple curves for the load-deformation data.

The fitting procedure may also be configured to address hysteresis exhibited by the load-deformation data. The hysteresis arises from the cyclical nature of the joint testing. The load-deformation data may thus have a respective curve, or curve segment, for each direction of joint movement (e.g., increasingly external or internal in an external-internal rotation test). Each direction of the cyclical testing may thus be fitted separately. Alternatively or additionally, the curve segments are averaged.

During the testing of a knee joint, a load or torque is applied to the tibia from a position distal to the foot. While the test is in progress, information from the testing apparatus is collected such that a load-deformation curve along each of the six degrees of freedom, i.e., X-translation, X-rotation, Y-translation, Y-rotation, Z-translation and Z-rotation, can be constructed. The primary motion of the tibia occurs along the axis on which the load or torque is applied, e.g., if the load is applied around the tibial Z-axis, then the primary motion during the test is the tibial motion in internal and external rotation or around the tibial Z-axis. The secondary motions are in all of the other five degrees of freedom not in the primary motion, e.g., X-translation, Y-translation, Z-translation, X-rotation and Y-rotation. When all six of these load-deformation curves are combined into one data set it can be said to describe the kinetic/kinematic function unique to one knee. Each load-deformation curve represents a principle component in the analysis of function of that one knee. From each of these two dimensional plots, single features or a family of features can be extracted or otherwise determined. The features can collectively describe each of these principal components. Furthermore, each of these load-deformation curves can be used to estimate a first and second order derivative curve. Each one of these curves can contain information that can be singularly separated out as a feature to describe unique characteristics of that particular principle component. Various collections of these 'descriptors' or 'features' can be utilized to develop a profile or other dataset defining or otherwise representative of a particular ligament injury or other joint condition.

The biomechanical characteristic(s) identified via the analysis may be combined with other information to evaluate or assess the condition or status of the joint under test. A profile of characteristics may be compiled to avoid undue reliance on a single factor, parameter, or characteristic (e.g., curve shape, endpoint slope, point-wise comparisons, etc.). The profile may then be compared with preset profile data associated with normal and abnormal joints to determine, for instance, a particular type of surgical or non-surgical treatment. A wide variety of information other than characteristics derived from the curve may be incorporated into the profile, including, for instance, data not captured by the robotic testing apparatus, such as characteristics of the bone structure(s) of the joint.

Various combinations of descriptors or other features of a joint under test can be analyzed together as a mechanical system. Under the guidelines of control theory, conditions of the joint can be tested or evaluated using the descriptors or features in a procedure to determine when and if the joint is or will become unstable, e.g., when the distal femur and the proximal tibia do not articulate in a normal or 'healthy fashion' or when patients have subjectively described instability or when a clinician can reproduce the aforementioned positive 'pivot shift' test.

Although described in connection with a number of examples involving knee testing and evaluation, the disclosed systems and methods are not limited to a particular type of joint. The systems and methods are also not limited to particular types of tests. The nature of the tests may vary considerably in conjunction with the type of joint being assessed or evaluated. The data from any number of tests may be combined or synthesized.

Although described in connection with a number of examples of a robotic testing apparatus, the source of the data obtained by the disclosed systems and methods may vary. A variety of different test devices and equipment may be used in conjunction with, and/or as part of, the disclosed systems and methods. As described below, the nature of the data acquired by the test equipment may vary as well.

Turning now to the drawings, FIG. 1 shows a robotic testing apparatus 50 in accordance with one example. In this case, the robotic testing apparatus 50 is an RKT apparatus. Details regarding examples of the RKT apparatus 50 are described in U.S. Patent Publications Nos. 2014/0081181 and 2012/0046540, the entire disclosures of which are hereby incorporated herein by reference.

The RKT apparatus 50 of FIG. 1 generally has a patient support or, as identified herein, a table assembly 52. The RKT apparatus 50 also has a robotic mechanism or limb manipulation device, identified for ease of description herein as a robot 54, positioned at one end or edge of the table assembly. The table assembly 52 in this example has a supporting frame that is identified herein as a base 56 beneath a patient platform 58. The base 56 is configured to rest on a floor or surface and to support the patient platform 58 above the floor. The patient platform 58 can include a substantially rigid or sturdy panel (not shown) capable of holding and supporting a patient thereon. The panel can be affixed to or otherwise supported by the base 56. The panel of the patient platform 58 can underlie a padded surface 60, which can include a textile or fabric material that covers a cushion, padding, or the like (also not shown).

As will be evident to those having ordinary skill in the art, the configuration and construction of the table assembly 52 can vary considerably from the example disclosed, illustrated, and briefly described herein. The base 56 and/or the patient platform 58 can each be altered in size, shape, orientation, height, construction, materials, and the like. The base can include multiple legs and frame elements that are assembled or connected to one another, as in the illustrated example. Alternatively, the base can be formed as one unitary support element. The patient platform can also be formed of multiple components and can be fastened to or otherwise attached to the base. Alternatively, the patient platform can an integral, one piece fabricated structure and can be fabricated as part of the base or attached thereto. The table assembly need not be a table, but instead can be a chair, a suspension system, or other suitable patient support that is capable of properly positioning and retaining a patient relative to the robot 54 for testing and examination. The table assembly 52 can further include additional features, though not disclosed or described herein, that may be used to assist in positioning a patient on the platform, to assist in maintaining a patient's position on the platform, or to otherwise enhance patient comfort or improve performance of the table assembly, the RKT apparatus, or both.

With reference to FIG. 1, the robot 54 in this example can include a main or primary support frame structure, identified herein for ease of description as a frame 62. The frame 62 may optionally be coupled to, a part of, or otherwise supported by or connected to a portion of the base 56 of the table assembly 52, as shown in FIG. 1. Alternatively, the frame of the robot 54 can be an extension of, connected to, or otherwise supported by a portion of the patient platform 58. In a further alternative, the frame can be some combination of such supporting structures and arrangements or can be a completely separate structure. In any case, the frame 62 in this example supports and positions the robot 54 of the RKT apparatus 50 at one end of the table assembly 52.

Figure 2:
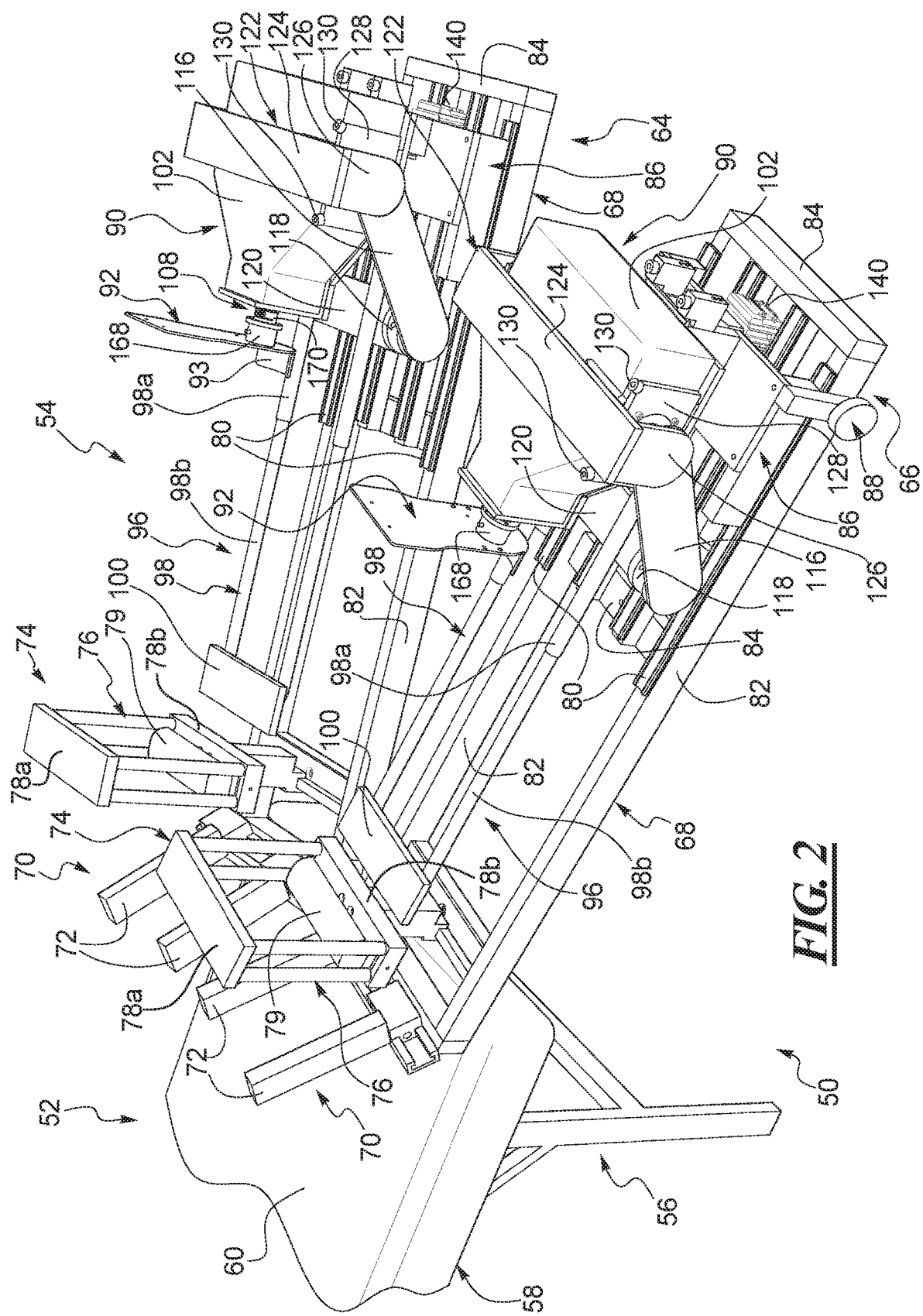
FIG. 2 shows an enlarged view of a limb evaluation device or robot of the RKT apparatus of FIG. 1.
Figure 3:
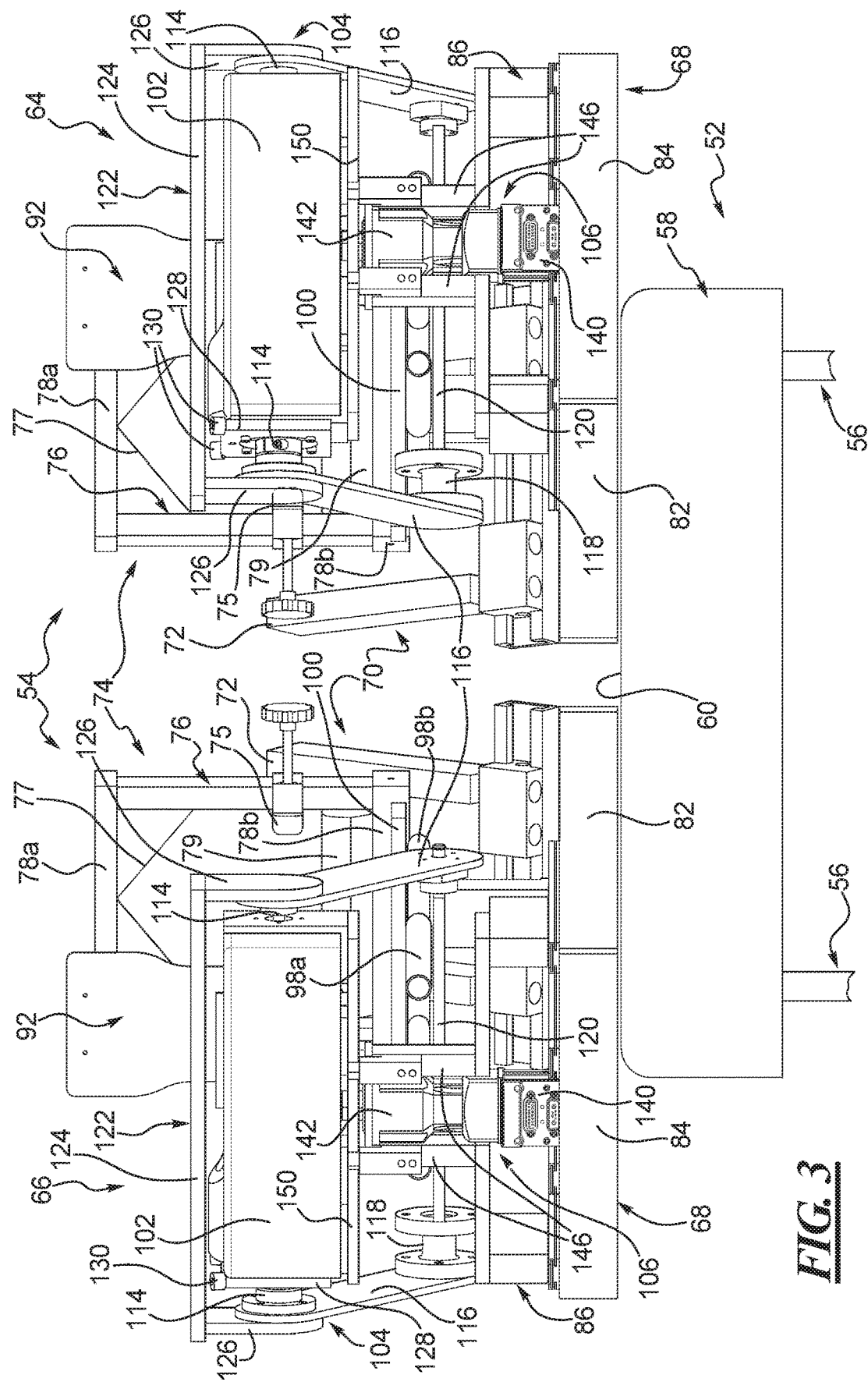
FIG. 3 shows an end view of the robot when viewed from the right hand side in FIG. 2.

In the disclosed example and with reference to FIGS. 2 and 3, the robot 54 has a left leg testing and evaluation mechanism and a right leg testing and evaluation mechanism, each mechanism respectively identified herein as a left leg portion 64 and a right leg portion 66 of the robot. The left and right leg portions 64, 66 have substantially the same construction, and may be essentially identical, if desired, and each is constructed to support and evaluate a left leg and right leg, respectively, of a patient. Therefore, like reference numerals are used herein to identify common parts of each of the two leg portions 64, 66 that have the same construction. The left and right leg portions 64, 66 each have a sub-frame 68 that, in this example, is supported by the frame 62 of the robot 54. Each sub-frame 68 supports the components and parts of the corresponding left and right leg portions 64, 66. For ease of description, the right leg portion 66 of the robot 54 is described in more detail below with the understanding that the left leg portion 64 has or may have the same overall construction. Differences between the two leg portions are identified herein, if and as needed. It is possible that an RKT apparatus is provided that has only one leg portion for evaluating only one leg of a patient at a time. However, in the disclosed example, the RKT apparatus 50 has left and right leg portions 64, 66.

Figure 4:
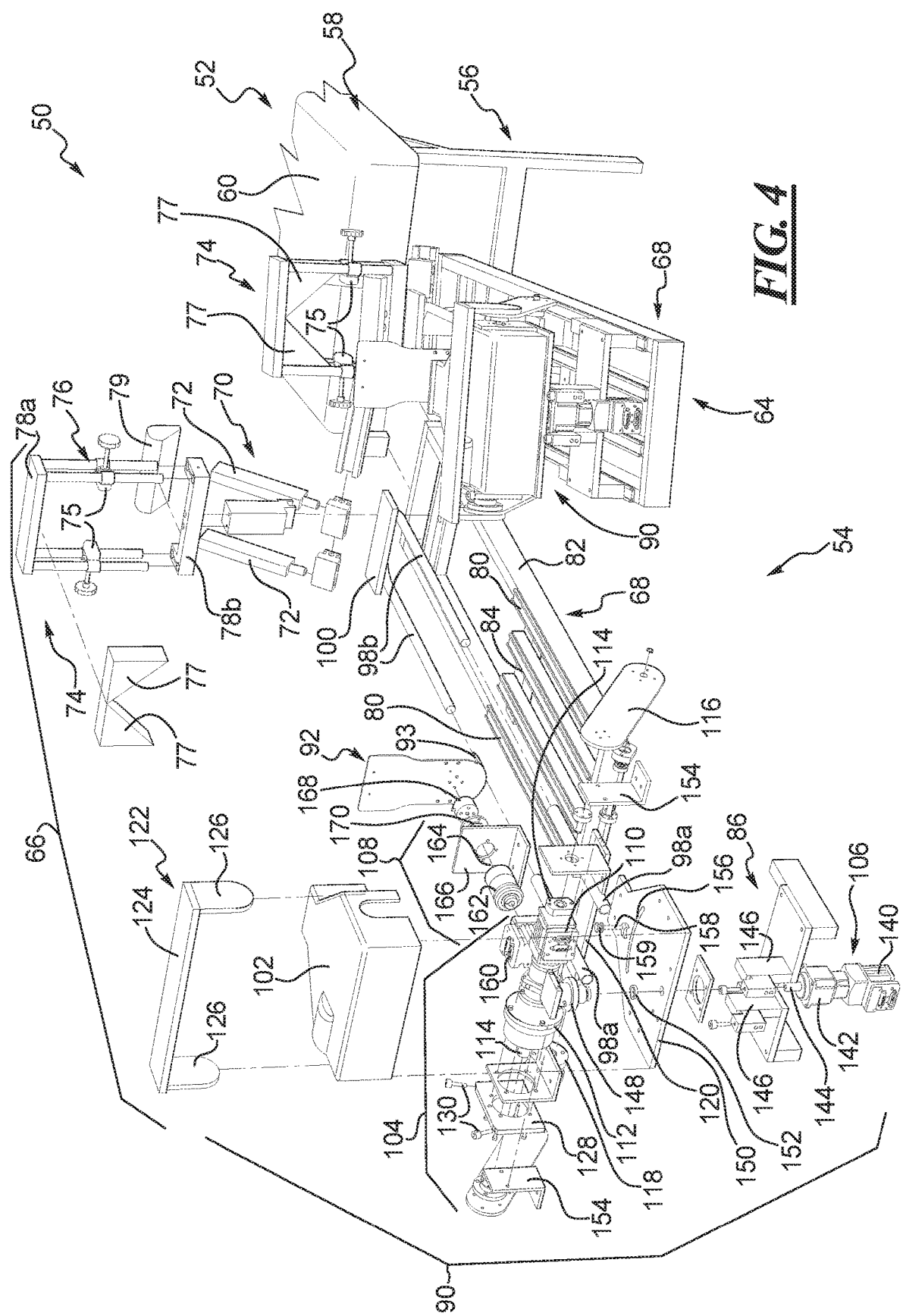
FIG. 4 shows a partial exploded view of the robot of FIG. 2 with the right leg portion of the robot exploded.
Figure 5:
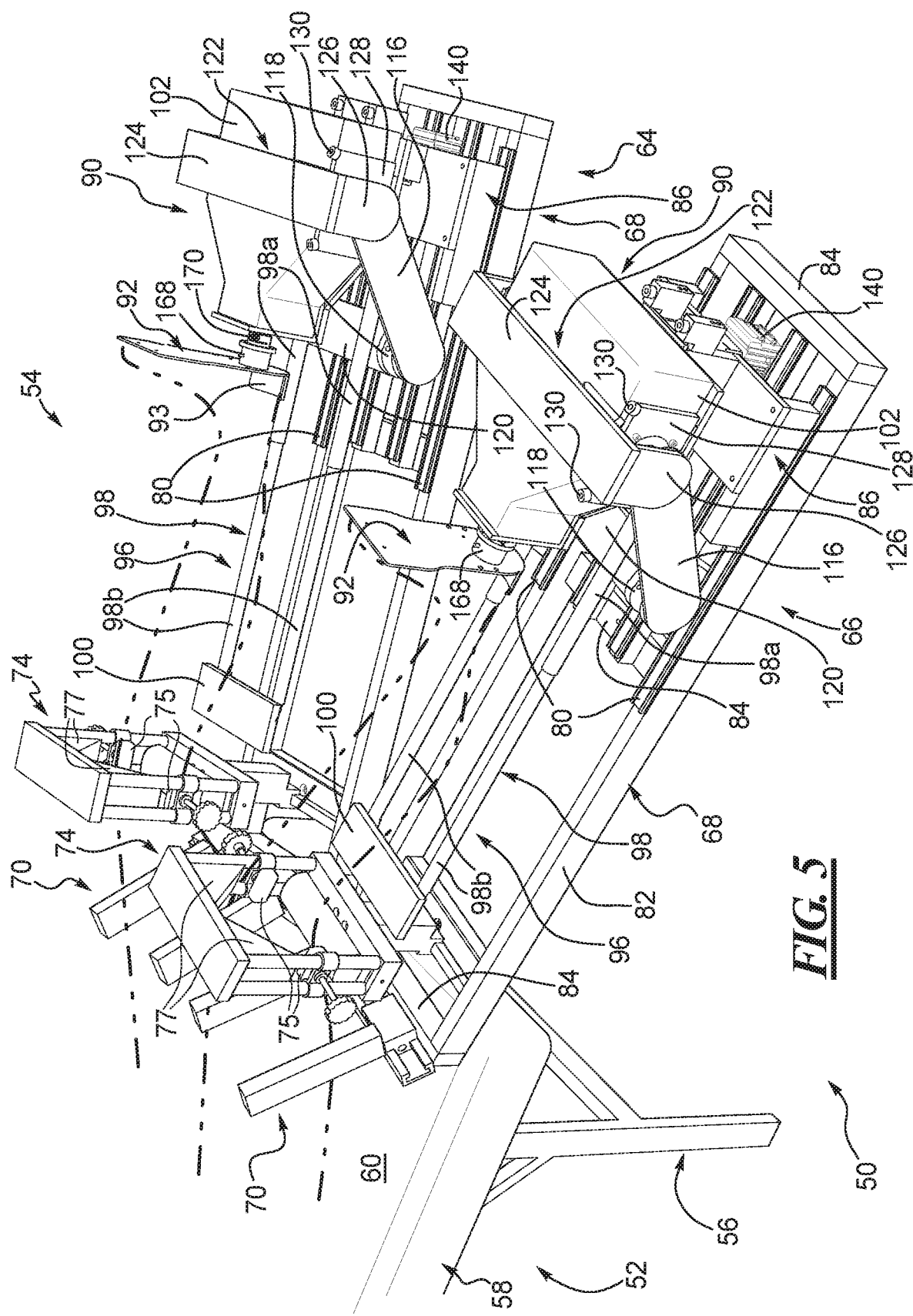
FIG. 5 shows the robot of FIG. 2 and depicts left and right legs of a patient positioned relative to the left and right leg portions of the robot.

As depicted in FIGS. 2-4, the right leg portion 66 has a thigh stabilizer 70 positioned closest to the table assembly 52. The thigh stabilizer 70 can be mounted to the frame 62 or the sub-frame 68, or can be otherwise mounted to a portion of the RKT apparatus 50 in a manner suitable for use as described below. The thigh stabilizer 70 can be constructed so as to be positionally adjustable to accommodate a wide range of patients of different size. Alternatively, the thigh stabilizer 70 can be mounted in a fixed position relative to the table assembly 52, whereby the position of the patient on the table assembly 52 and relative to the thigh stabilizer 70 might be adjustable. In either embodiment, the thigh stabilizer 70 should be positioned or positionable to contact a portion of a patient's upper leg or thigh above the knee, as depicted in FIG. 5.

The thigh stabilizer 70 in this example has a pair of femur clamping elements 72, i.e., medial and lateral clamping elements, that are laterally spaced apart and width-wise adjustable relative to one another. Though not shown herein, the clamping elements can include a pad or pads on the thigh facing surfaces, if desired, to provide a degree of comfort for a patient. The femur clamping elements 72 can be side-to-side adjusted in order to clamp or otherwise securely hold a patient's right femur and thigh in a substantially fixed side-to-side position during testing, evaluation, or treatment, as described below. If the thigh stabilizer 70 is positionally adjustable, it should be capable of being secured in a fixed selected position, once properly adjusted for a given patient, relative to the table assembly 52 and/or robot 54 during testing, evaluation, or treatment. The configuration and construction of the thigh stabilizer 70 can vary considerably from the example shown herein. The clamping elements 72 can be replaced by other suitable securing or clamping devices or elements and the mechanisms to adjust and secure the thigh stabilizer 70 can also vary.

The right leg portion 66 also has a knee stabilizer 74 positioned adjacent the thigh stabilizer. The knee stabilizer 74 can also be mounted to the frame 62 or the sub-frame 68, or can be otherwise mounted to a portion of the RKT apparatus 50 in a manner suitable for use as described below. The knee stabilizer 74 can optionally also be constructed so as to be lengthwise or longitudinally positionally adjustable to accommodate a wide range of patients of different size. The knee stabilizer can also be side-to-side adjustable as well. Alternatively, the knee stabilizer 74 can be mounted in a fixed position relative to the table assembly 52, whereby the position of the patient on the table assembly 52 and relative to the knee stabilizer 74 may be adjustable. In either embodiment, the knee stabilizer 74 should be positioned or positionable to contact the knee or patella at the lower end of a patient's femur and thigh, as depicted in FIG. 5.

The knee stabilizer 74 acts as a knee or patellar clamp and can include a framework 76 arranged to surround and clamp onto a patient's joint or knee. The knee stabilizer 74 in this example has a pair of patellar clamping elements, including an upper clamping element 78a and a lower clamping element 78b, that are vertically spaced apart and adjustable relative to one another along the framework 76. The patellar clamping elements 78a, 78b can be vertically adjusted in order to clamp or otherwise securely hold the lower end of a patient's right femur and patella in a substantially fixed vertical position during testing, evaluation, or treatment, as described below. If the knee stabilizer 74 is positionally adjustable, it should be capable of being secured in a fixed selected position, once properly adjusted for a given patient, relative to the table assembly 52 and/or robot 54 during testing. The configuration and construction of the knee stabilizer 74 can vary considerably from the example shown herein. The patellar clamping elements 78a, 78b can be replaced by other suitable securing or clamping devices or elements and the mechanisms to adjust and secure the knee stabilizer 74 can also vary.

Though not shown in all of the figures, the knee stabilizer 74 can include a plurality of substantially rigid and/or resilient pads for holding and restraining the knee and patella of a patient. In one example, the knee stabilizer knee can include a pair of side-to-side opposed Varus-valgus pads 75 that are adjustable, as shown and described below, toward and away from one another across the framework 76. The knee stabilizer 74 can also include one or more upper pads 77 on the upper clamping element 78a and a lower pad 79 on the lower clamping element 78b. The pads 75, 77, and/or 79 can be configured and arranged to lie adjacent the patient's knee. The various pads 75, 77, and 79 can be configured to prevent the framework 76 and the patellar clamping elements 78a, 78b from directly contacting the patient's knee, but also to assist in restraining the knee and inhibiting movement during testing. The pads 75, 77, and/or 79 can be solid, hollow, pressurized, hydraulically filled, pneumatically filled, or the like and can be rubber, foam, or otherwise formed of suitable materials. In one example as shown, the pad or pads 77 on the upper patellar clamping element 78a can be configured to define a V-shape within the framework 76. The patient's leg can then be captured within the V-shape as the upper and lower patellar clamping elements 78a, 78b are drawn toward one another to capture and hold the patient's leg still during a procedure. In particular, the stabilizer 74 and these pads 77 can aid in constraining the patella during testing. The Varus-valgus pads 75 can also be adjusted to restraint movement of the patient's knee in a side-to-side direction during at least Varus-valgus testing, as described below.

The thigh stabilizer 70 and/or the knee stabilizer 74 may be mechanically adjustable to manually fit and accommodate different sized patients. In one alternative, the thigh stabilizer 70 and/or the knee stabilizer 74 may be electrically operable to adjust the femur clamping elements 72, the patellar clamping elements 78a, 78b, respectively, or both. In another alternative example, the femur clamping elements 72 and/or the patellar clamping elements 78a, 78b may be pneumatically or hydraulically operable to adjust the thigh and knee stabilizers 70 and 74. In yet another alternative, the thigh stabilizer 70, the knee stabilizer 74, or both, may include two or more such systems or mechanisms for adjusting the respective clamping elements.

The thigh stabilizer 70 and/or femur clamping elements 72 and the knee stabilizer 74 and/or framework 76 and patellar clamping elements 78a, 78b can be formed of metal, plastic, or other suitable materials. The thigh and knee stabilizers 70 and 74 can vary in shape, configuration and construction, as desired. The thigh and knee stabilizers 70 and 74, in combination, are intended to secure a patient's leg in order to hold the femur and patella in a vertically (knee stabilizer) and laterally (thigh stabilizer) fixed position during a test, evaluation, or treatment cycle. Features and aspects of the disclosed thigh and knee stabilizers 70 and 74 can vary considerably while accomplishing this objective.

In this example as shown in FIGS. 2 and 4, the sub-frame 68 is configured to define or carry one or more slide tracks 80. The track or tracks 80 can be carried on the free end of the sub-frame 68 that is distal or spaced from the table assembly 52. The sub-frame 68 is formed having a plurality of rails 82 that extend lengthwise and having one or more cross-members 84 that extend laterally between the rails. The tracks 80 can be formed as an integrated part of the rails 82 or other sub-frame components or, as in this example, can be separately mounted to or supported by the rails and/or cross-members 84. One or more trucks or carriages, hereinafter a sled assembly 86 is mounted on or supported by the sub-frame 68 and is slidable along the tracks 80. The sled assembly 86 can slide along the tracks 80 to adjust the position of various parts of the RKT apparatus 50, as described further below. The sled assembly 86 can include a locking mechanism 88 (shown only in FIG. 2) to secure the sled assembly in a desired or selected position along the tracks 80. The locking mechanism 88 can vary in construction and position on the apparatus, as long as it can adequately secure the sled assembly at a selected position. Adjustment of portions of the RKT apparatus 50 can be achieved in other ways. In one example, the RKT apparatus can be mounted to a lift that can raise or lower the apparatus, or portions thereof, and that can slide or roll the robotic components relative to the table assembly 52, either eliminating or altering the need for the tracks 80 and rails 82.

As depicted in FIGS. 2-4, the right leg portion 66 further includes a tibia positioning assembly 90 that is mounted on the sub-frame 68. In this example, the tibia positioning assembly 90, or at least a portion of the assembly, is carried on the sled assembly 86. Thus, the tibia positioning assembly 90, or at least a portion thereof, is slidable lengthwise along the tracks 80 of the sub-frame 68 on the sled assembly 86, and thus is movable relative to the table assembly 52 and/or to the thigh and knee stabilizers 70 and 74.

In general, the tibia positioning assembly 90 has a foot holder, which in one example can be a foot plate 92, as in this example. The foot plate 92 has a heel stop 93 at the bottom edge of the foot plate that faces upward and has a contact surface 94 that faces toward the thigh and knee stabilizers 70 and 74. The tibia positioning assembly 90 also has a tibia rod device 96 with one or more rods 98 and a calf contacting or loading portion, which in one example can be a calf plate 100 as in this example. The calf plate 100 is disposed at or near a distal end of the tibia rod device 96. The one or more rods 98 can be lengthwise adjustable. In this example as shown in FIGS. 2-4, the tibia rod device 96 has two tibia rods 98, each of which has two telescoping segments including a fixed segment 98a and a slidable segment 98b that permit length adjustment of the rods 98. Though not shown or described in detail herein, the rods 98 may include a locking mechanism of a suitable type, such as holes and set screws, VALCO ball devices, or the like on one or both of the segments 98a, 98b, that can lock the adjusted rods at a selected length. The telescoping segments permit adjustable positioning of the calf plate 100 relative to the foot plate 92 to accommodate different sized patients. During use, the calf plate 100 lies under and contacts a patient's calf below the knee and the foot plate 92 bears against the sole of the patient's foot. The foot plate 92 can be configured to physically constrain and hold the foot of a patient against the contact surface 94. In one example, though not shown herein, the foot plate 92 can employ one or more straps that secure the patient's heel against the heel stop 93 and the sole of their foot to the foot plate 92. Likewise, the calf plate 100 can be configured to physically constrain the patient's leg to the calf plate, as described below for certain tests, or can merely lie against and under the patient's calf while not being otherwise secured to the leg for other tests.

Figure 6:
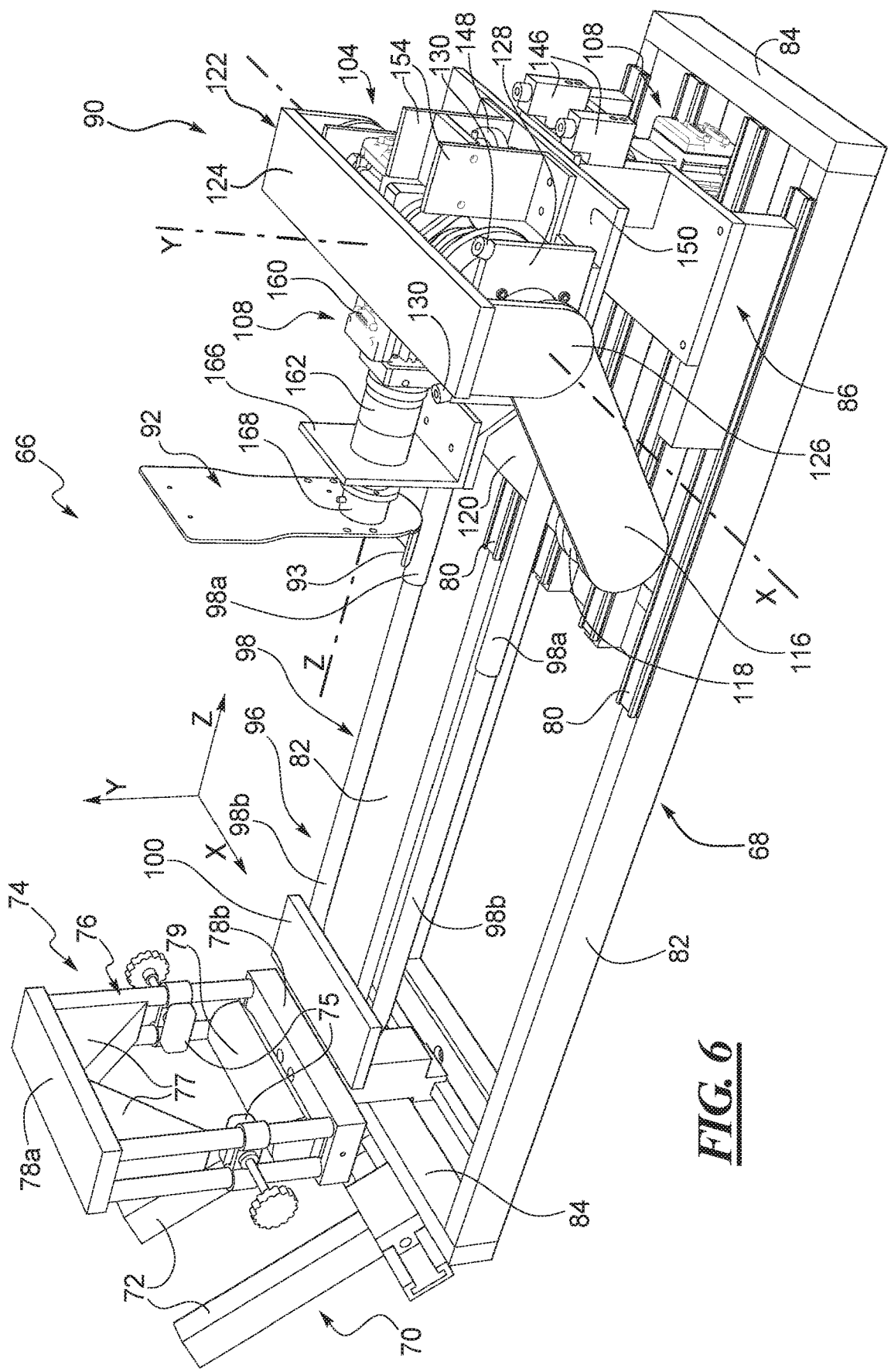
FIG. 6 shows the right leg portion of the robot of FIG. 2 and depicts an X-Y-Z coordinate system defined by the right leg portion.

With reference to FIGS. 4 and 6, the tibia positioning assembly 90 has a drive system with a number of drive components configured to impart specific and controllable movements to the lower leg of a patient. In this example, a substantial number of the drive system components are housed within a shell or housing 102. In other examples, the drive system components may be exposed and the shell eliminated. The drive system in this example generally has a first drive, i.e., an X-axis drive 104 as identified herein, which is oriented to define and provide rotation about a first axis, i.e., an X-axis as identified herein, which in this example lies generally laterally across the tibia positioning assembly 90. The drive system also has a second drive, i.e., a Y-axis drive 106 as identified herein, which is oriented to define and provide rotation about a second axis, i.e., a Y-axis as identified herein, which in this example lies generally vertically through the tibia positioning assembly 90, though not quite intersecting the X-axis, as described below. The drive system further has a third drive, i.e., a Z-axis drive 108 as identified herein, which is oriented to define and provide rotation about a third axis, i.e., a Z-axis as identified herein, which in this example lies lengthwise along the tibia positioning assembly 90. The three axes define a coordinate system and this coordinate system is identified as an X-Y-Z coordinate system for the right leg portion 66 of the robot 54 in this example. The robot will also have a similar X-Y-Z coordinate system specific to the left leg portion 64, but independent of the coordinate system for the right leg portion 66.

In other examples, the RKT apparatus may be configured to test only one or two of anterior-posterior motion, Varus-valgus motion, or tibial rotation, instead of all three tests. In such cases, the drive system may include only one or two of the X-axis, Y-axis, or Z-axis drives instead of all three drives. The methods and procedures described herein may be modified to accommodate such robots that have fewer than all three drives. In other examples, the X-Y-Z axes of the aforementioned coordinate systems may all intersect with one another and may all be orthogonal to one another. In still other examples, none or only two of the axes may intersect and/or none or only two of the axes may be orthogonal to one another.

As shown in FIG. 4, the X-axis drive 104 can include a first motor, such as an electric motor 110, a gearbox 112, and an output shaft 114 that is driven by the motor and gearbox. The opposite ends of the output shaft 114 in this example are fixedly coupled to the upper ends of respective drive links 116 on opposite sides of the housing 102. Thus, as the output shaft 114 is rotated by the motor 110 and gearbox 112, the drive links 116 are also rotated about the X-axis. The drive links 116 in this example are oriented downward and forward from the X-axis. The lower end of one of the drive links 116 is coupled or fixed to an X-axis torque transducer 118. The torque transducer 118 is also coupled or fixed to one end of a cross-plate 120. The lower end of the other drive link 116 is fixed to the opposite end of the drive plate 120. The cross-plate 120 is coupled to and extends laterally across the right leg portion 66 forward of the X-axis between the drive links 116. In this example, the fixed segments 98a of the tibia rods 98 are fixedly mounted to and extend forward toward the knee and thigh stabilizers 70, 74 from the cross-plate 120, as shown in FIGS. 2 and 4.

Figure 7:
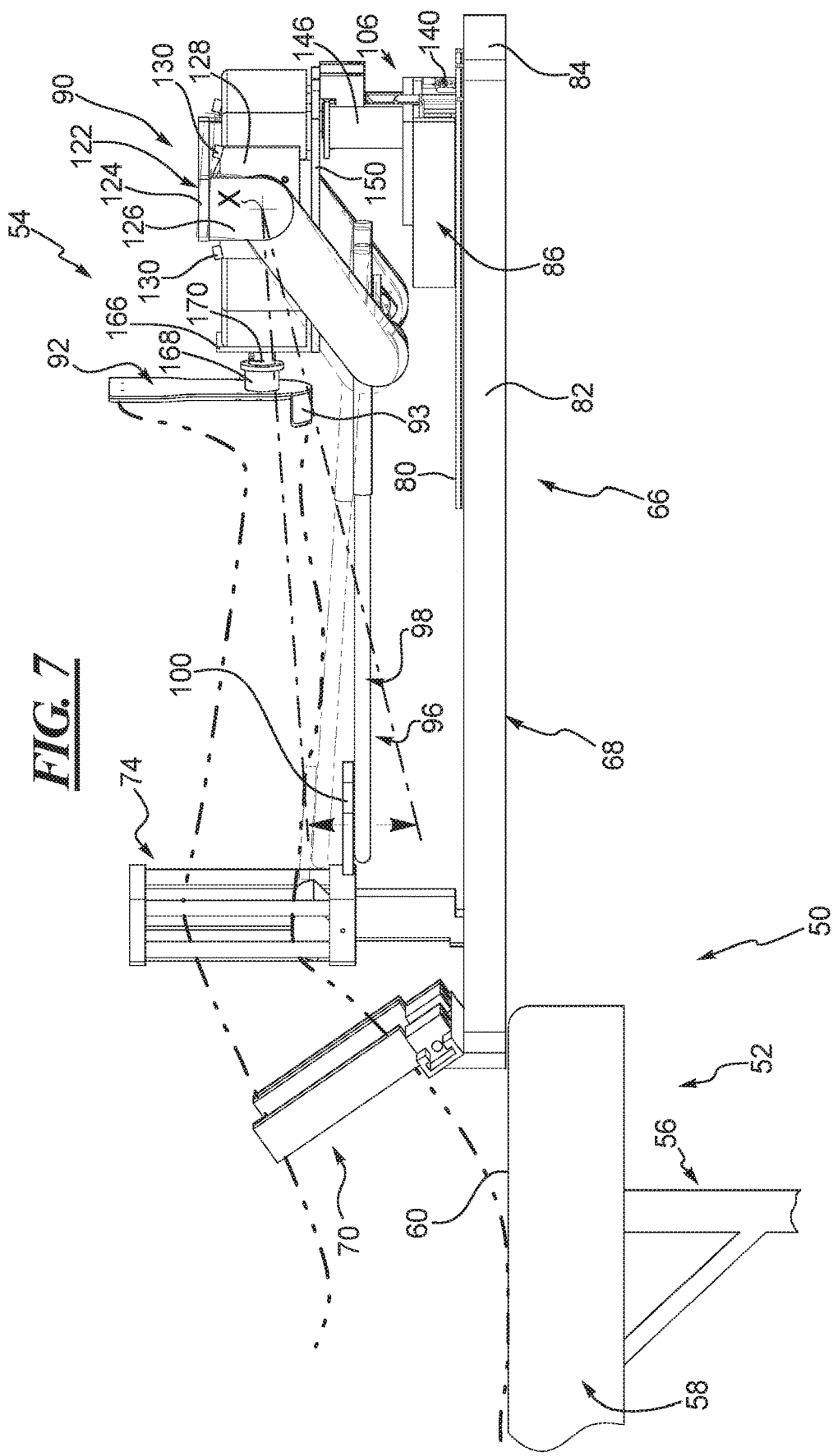
FIG. 7 shows a side view of the robot of FIG. 5 and illustrates anterior-posterior motion of the robot about the X-axis of the right leg portion of the robot.

With reference to FIG. 7, the X-axis drive 104 is configured to conduct an anterior-posterior or A-P test on a patient's knee. Position sensors can be applied to appropriate locations on the right leg of the patient. The X-axis drive 104 imparts force about the X-axis to initiate anterior-posterior motion in the tibia part of the knee joint relative to the fixed femur part of the knee joint of the patient, as shown in FIG. 7. The motor 110 can reversibly rotate the output shaft 114 through an arc about the X-axis whereby the upper ends of the drive links 116 are rotated through the same arc. This in turn moves, i.e., raises or lowers the lower ends of the drive links 116, which in turn raises or lowers the cross-plate 120 and the fixed segments 98a of the tibia rods 98. Movement of the fixed segments 98a of the tibia rods 98 raises or lowers the slider segments 98b and thus the calf plate 100 carried on the tibia rods 98. The X-axis torque transducer 118 measures the applied torque at the cross-plate 120 caused by the load applied at the calf plate 100 as the calf plate pushes up on the patient's tibia or the tibia rods 98 pull down on the patient's tibia. Motion and load data can be collected by a processor from the sensors relative to the motion in the patient's leg and from the X-axis torque transducer 118 relative to the torque or applied force.

The motor 110 and/or gearbox 112 can be designed to produce a limited range of travel, which may be substantially less than 360 degrees of rotations, in the output shaft 114. In addition or in the alternative, the X-axis drive 104 can also be designed to incorporate a mechanical travel limiter, if desired. In one example as shown in FIGS. 3, 4, 6, and 7, a yolk assembly 122 can be provided as part of the X-axis drive 104. The yolk assembly 122 has a top plate 124 extending over a top of the housing 102. The yolk assembly 122 also has a pair of side plates 126 extending down from the top plate 124. The side plates 126 can be affixed to the upper ends of the drive links or otherwise to the drive shaft 114 of the motor 110, so that the yolk assembly 122 also rotates with the drive shaft. A stop bracket 128 is disposed at one end of the motor 110 adjacent one of the yolk side plates 126. Two stops 130, i.e., fore and aft travel stops protrude upward from the stop bracket 128. The stops 130 are positioned and circumferentially spaced apart relative to the X-axis. The top plate 124 of the yoke assembly 122 is captured between the two stops and hits one of the stops to limit travel of the yoke assembly in either rotation direction. The radius of the side plates 126 and spacing of the stops 130 can thus limit rotational travel of the output shaft 114 to a specific arc, which mechanically limits the upward and downward travel of the tibia rods 98.

The above-described anterior-posterior movement components of the tibia positioning assembly 90 can vary considerably from the example shown and described herein. The yoke assembly 122 and stop bracket 128 can be eliminated or can take on different positions, configurations, and constructions. Instead, another mechanical stop mechanism can be employed. Likewise, the configuration and construction of the drive links 116, cross-plate 120, tibia rods 98, and calf plate 100 can also be varied. The mechanisms or devices that are used to secure a patient's leg to the tibia rods 98 and to the foot plate 92, if and when needed for testing, can also vary.

As shown in FIGS. 4 and 6, the Y-axis drive 106 can also include a second motor, which can also be an electric motor 140, a gearbox 142, and an output shaft 144 that is driven by the motor and gearbox. The gearbox 142 and motor 140 are fixed to the sled assembly 86 beneath the X-axis drive 104. Thus, the entire tibia positioning assembly 90, including the Y-axis drive components, can slide lengthwise along the sub-frame 68 to adjust the foot plate 92 position relative to the table assembly 52 and/or the thigh and knee stabilizers 70, 74. The motor 142 can be secured to a motor mount or bracket 146 that is carried on the sled assembly 86. A Y-axis torque transducer 148 is fixed to the output shaft 144 for rotation therewith. A pivot plate 150 can be sandwiched between a pair of thrust bearings 152 with the Y-axis drive below the pivot plate and the Y-axis torque transducer above the pivot plate. Support brackets 154 are secured to the top of the pivot plate 150 and the torque transducer 146 is fixed to the support brackets. The pivot plate 150 is disposed on top of the motor mounts 146 in this example and can rotate relative to the mounts and the sled assembly 86. The shell 102 can be secured to the pivot plate 150 to create an enclosure for the X-axis drive 104 and the Z-axis drive 108. Thus, as the output shaft 144 is reversibly rotated by the motor 140 and gearbox 142 about the Y-axis, as represented in FIG. 8, the shell 102, pivot plate 150, X-axis drive 104, Z-axis drive 108, foot plate 92, and tibia rods 98 will all rotate about the Y-axis.

Figure 8:
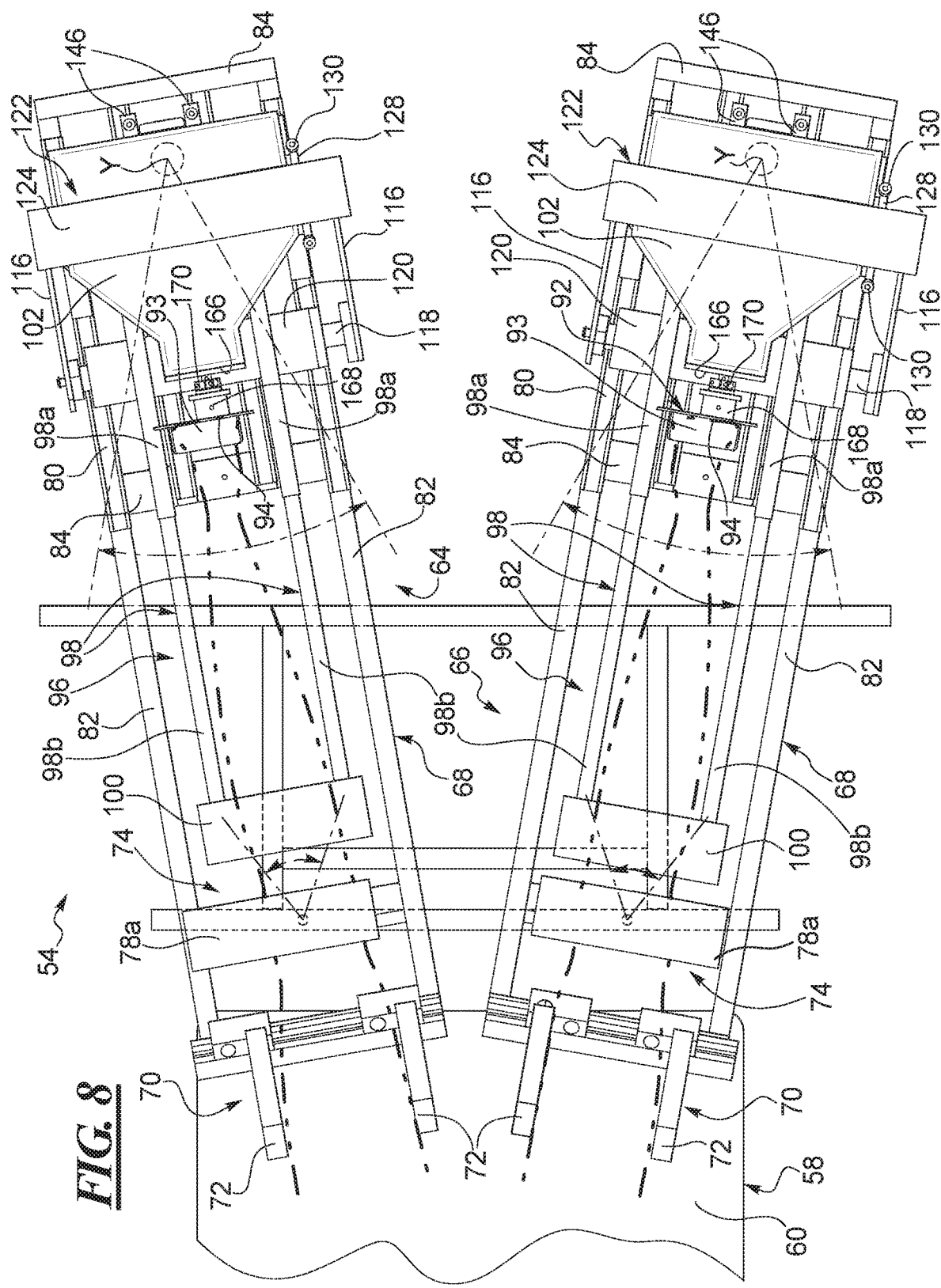
FIG. 8 shows a top view of the robot of FIG. 5 and illustrates Varus-valgus motion of the robot about the Y-axis of each of the left and right leg portions of the robot.

As represented in FIG. 8, the Y-axis drive 106 is configured to conduct a Varus-valgus or V-V test on a patient's knee. Position sensors can be applied to appropriate locations on the right leg of the patient. The Y-axis drive 106 imparts force about the Y-axis to initiate Varus-valgus motion in the tibia part of the knee joint relative to the fixed femur part of the knee joint of the patient, as shown in FIG. 8. The motor 140 can reversibly rotate the output shaft 144 through an arc about the Y-axis whereby the pivot plate 150 is rotated through the same arc. This in turn moves, i.e., pivots the Z-axis drive 108 side-to-side, which in turn pivots the foot plate 92 and the tibia rods 98 about the Y-axis. Movement of the tibia rods 98 moves the patient's lower leg side-to-side relative to the femur. The Y-axis torque transducer 148 measures the applied torque at the output shaft 144 caused by the load applied at the calf plate 100 or along the tibia rods as the tibia rods push the patient's tibia medially or laterally relative to the femur. Motion and load data can be collected by a processor from the sensors relative to the motion in the patient's leg and from the Y-axis torque transducer 148 relative to the torque or applied forces.

The motor 140 and/or gearbox 142 can be designed to produce a limited range of travel, which may be substantially less than 360 degrees of rotations, in the output shaft 114. In addition or in the alternative, the Y-axis drive 108 components can also be designed to incorporate a mechanical travel limiter, if desired, though not shown or described herein.

The above-described Varus-valgus movement components of the tibia positioning assembly 90 can also vary considerably from the example shown and described herein. The sled assembly 86, motor mounts 146, pivot plate 150, and support brackets 154 can be eliminated or can take on different positions, configurations, and constructions. For example, the pivot plate 150 can include a curved guide slot 156 formed through the plate, as shown in FIG. 4. The guide slot 156 can be spaced a radial distance from the Y-axis and the output shaft 144 of the motor 140. A guide post 158 can be fixed to the sled assembly 86 and project upward toward the guide slot 156. A tip 159 of the guide post 158 can be captured in or seated in the guide slot and can be configured to both support the pivot plate 150 thereat and to slide along the guide slot as the pivot plate is rotated by the motor 140. Likewise, the configuration and construction of the cross-plate 120, tibia rods 98, calf plate 100, shell 102, and the like can also be varied. The mechanisms or devices that are used to secure a patient's leg to the tibia rods 98 and to the foot plate 92, if and when needed for testing, can also vary.

As shown in FIGS. 4 and 6, the Z-axis drive 108 can also include a third motor, which can also be an electric motor 160, a gearbox 162, and an output shaft 144 that is driven by the motor and gearbox. The gearbox 162 and motor 160 are fixed to a motor mounting bracket 166 that is attached to a front end of the pivot plate 150 and forward of the X-axis drive 104. In this example, the Z-axis is aligned with both the X-axis and the Y-axis, though in other examples this might not be the case. The entire Z-axis drive, including the foot plate 92, can also slide lengthwise along the sub-frame 68 to adjust the foot plate 92 position relative to the table assembly 52 and/or the thigh and knee stabilizers 70, 74 as noted above. A Z-axis torque transducer 168 is fixed to the output shaft 164 by an adaptor 170 for rotation therewith. In this example, the motor 160 and gearbox 162 are positioned behind the motor mounting bracket 166 and the adaptor 170 and torque transducer 168 are disposed forward of the mounting bracket. The enclosure defined by the shell 102 and the pivot plate 150 house the Z-axis drive 108, other than the foot plate 92, as noted above. The foot plate 92 is secured to the torque transducer 168 for rotation therewith. Thus, as the output shaft 164 is reversibly rotated by the motor 160 and gearbox 162 about the Z-axis, as shown in FIG. 9, the foot plate 92 will all rotate about the Z-axis.

Figure 9:
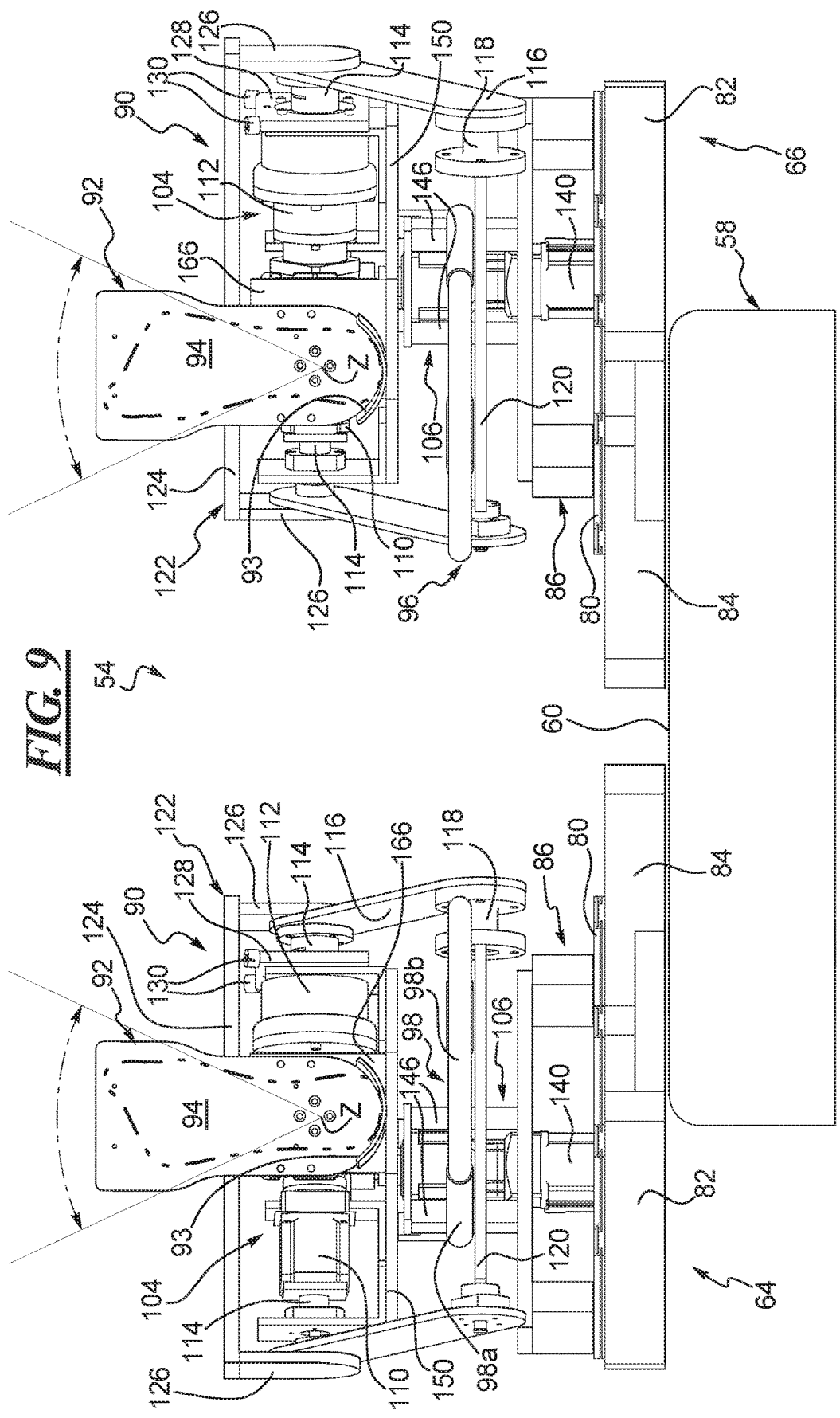
FIG. 9 shows an end view of the robot of FIG. 5 from the point of view and in the direction of the arrow IX and illustrates internal and external rotation of the robot about the Z-axis of each of the left and right leg portions of the robot.

As represented in FIG. 9, the Z-axis drive 108 is configured to conduct an internal and external rotation or simply a tibia rotation test on a patient's knee. Position sensors can be applied to appropriate locations on the right leg of the patient. The Z-axis drive 108 imparts force about the Z-axis to initiate rotation motion in the tibia part of the knee joint relative to the fixed femur part of the knee joint of the patient, as shown in FIG. 9. The motor 160 can reversibly rotate the output shaft 164 through an arc about the Z-axis whereby the adapter 170 and torque transducer 168 are rotated through the same arc. This in turn moves, i.e., rotates the foot plate 92 about the Z-axis. Movement of the foot plate 92 in this manner rotates the patient's lower leg internally and externally relative to the femur. The Z-axis torque transducer 168 measures the applied torque at the output shaft 164 caused by the load applied at the foot plate 92 as the foot plate rotates the patient's tibia or lower leg internally and externally relative to the femur. Motion and load data can be collected by a processor from the sensors relative to the motion in the patient's leg and from the Z-axis torque transducer 168 relative to the torque or applied forces.

The motor 160 and/or gearbox 162 can be designed to produce a limited range of travel, which may be substantially less than 360 degrees of rotations, in the output shaft 164. In addition or in the alternative, the Z-axis drive 108 components can also be designed to incorporate a mechanical travel limiter, if desired. A simple mechanical stop can be positioned to stop movement of the foot plate 92 in either rotation direction, if desired. Such a sop can be the tibia rods 98 or something mounted thereto. Alternatively, such a stop can be applied to the motor mounting bracket 166 or the like.

The above-described rotation movement components of the tibia positioning assembly 90 can also vary considerably from the example shown and described herein. The foot plate 92 and motor mounting bracket 166 can be eliminated or can take on different positions, configurations, and constructions. The mechanisms or devices that are used to secure a patient's leg to the foot plate 92, if and when needed for testing, can also vary.

The above described motors, gearboxes, and output shafts can also vary within the scope of the disclosure. The motors can be servo-motors or other types of motors suitable for precise motion and torque control and for the loads to which the motors will be exposed during such limb testing and evaluation. Any of the first, second, or third, i.e., X-, Y-, or Z-axis, drives with respect to the motors and gearboxes can be structurally configured substantially the same relative to one another, with the only substantive difference being the relative axis of rotation about which each is oriented. Alternatively, each drive can incorporate a motor and/or gearbox that is different than one or both of the others as well. The torque transducers can be selected in order to provide torque readings as known in the art relating to each of the three drives. In other examples, one or more of the torque transducers may be replaced with other torque or load sensors or load sensing means. For example, motor current may be measured to determine the torque or load on the motor output shaft during use. Any suitable means for modeling torque may be used. The torque readings can be calibrated and calculated as needed to correspond to known torque or force values imparted to a patient's limb(s). Movement of the patient's body parts may be detected by non-invasive systems, as noted above, that utilize sensors or markers that are attached to the skin, including but not limited to vision, optoelectronic, ultrasonic, and electromagnetic motion analysis systems.

In use, a patient lies on the padded surface 60 of the platform 58 on the table assembly 52 as shown in FIG. 5. The patient's knees are positioned to engage the knee stabilizers 74, their thighs are positioned to engage the thigh stabilizers 70, their feet are positioned to engage the foot plates 92, and their calves are positioned to engage the tibia rods. The patient can then be secured to the foot plates, to the knee stabilizers, and to the thigh stabilizers for testing and evaluation. The patient's calves or tibias can also be secured to the tibia rods 98, as needed for specific testing. Movement of the lower leg of the patient may be detected by non-invasive systems utilizes sensors or markers that are attached to the skin, including but not limited to optoelectronic, ultrasonic, and electromagnetic motion analysis systems. In one example, the RKT apparatus can be configured so that the patient's knees are flexed to about 30 degrees between the femur and the tibia. However, the tests or evaluations may also include the additional capability to flex the knee from 0 to 90 degrees to allow for similar tests (such as the examples above) done for different degrees of knee flexion.

Any one of the X-, Y-, and Z-drives can be decoupled from any of the other two. In the disclosed example, each of the three drive assemblies may be operable with one or more of the other at the same time or can be decoupled from each of the other two and be operable independent of the other two. In other examples, two or more, and perhaps all three of the drives can be mutually coupled relative to one another such that movements are substantially simultaneously imposed upon the patient's legs during use of the RKT apparatus. The combined simultaneous operation of two or all three of the motors allows the RKT apparatus to perform more complex testing, such as simulating the known manual pivot shift testing procedure.

The aforementioned sensors can be provided on the legs of a patient, in the power lines of the RKT apparatus, and/or on the X-, Y-, and Z drives to obtain desired position or location data as the lower leg is moved during testing and evaluation. The degree of movement of the patient's legs in the A-P test, the V-V test, and/or the rotation test can be measured by detecting the movements of the parts of the apparatus, the rotation of the drives, and/or the actual movements of the patient's legs. The torque encountered during each test and over the range of motion applied during each such movement may also be measured, suitably calibrated to the limb movement, and recorded. Various X-, Y-, and Z-axes can also be determined and recorded for and/or relating to the femoral and tibial axis of the patient for testing.

Figure 10:
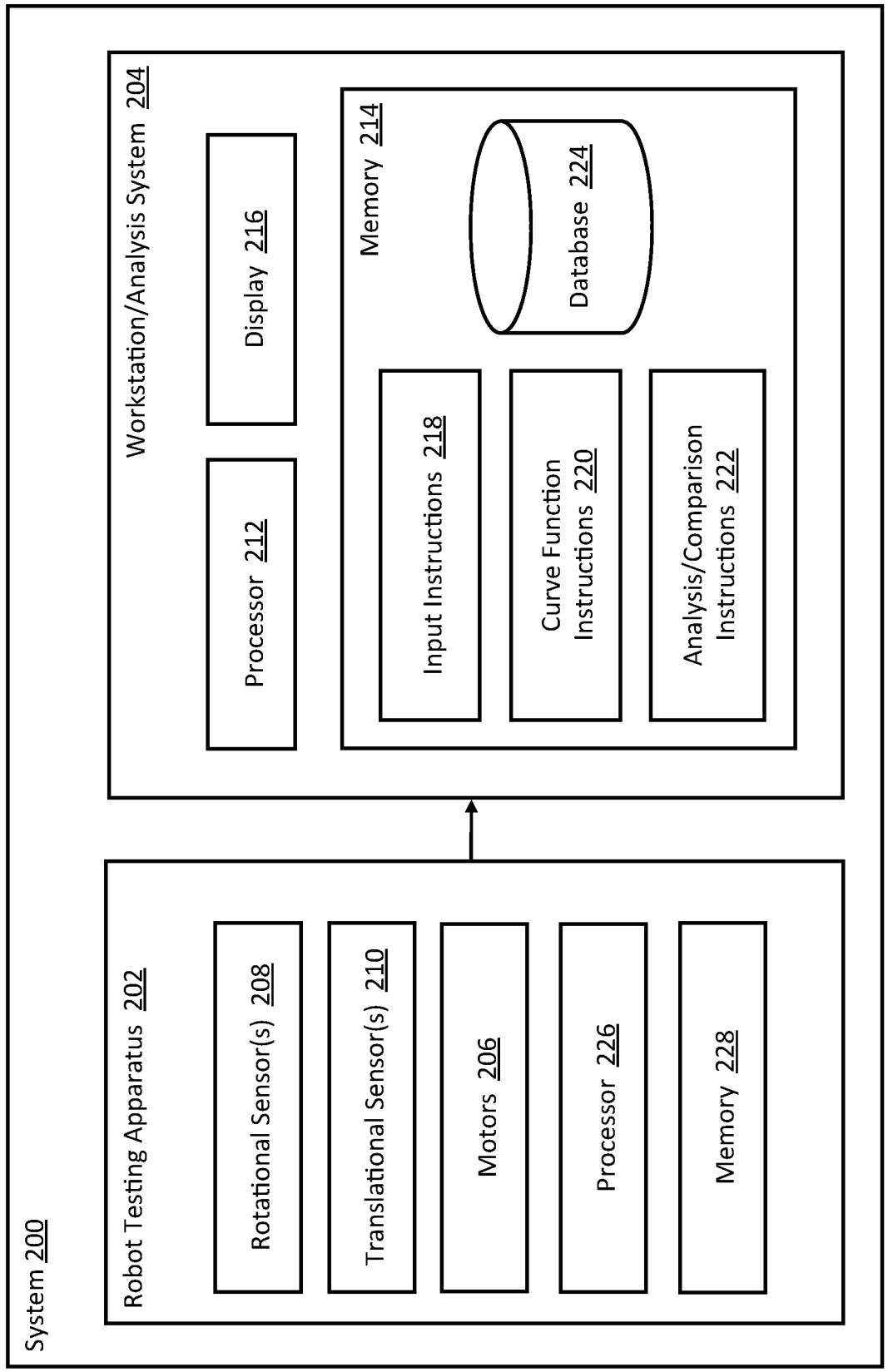
FIG. 10 is a block diagram of a system for curve function-based characterization and analysis of joints in accordance with one example.

FIG. 10 illustrates a system 200 directed to biomechanical characterization and analysis of knees and other joints. In this example, the system 200 includes a robot testing apparatus 202 and an analysis system 204 in communication with the robot testing apparatus 202. The analysis system 204 may be a workstation or other computer coupled to the robot testing apparatus 202. In this example, the communications and coupling between the robot testing apparatus 202 and the analysis system 204 are directed to providing data acquired by the robot testing apparatus 202 to the analysis system 204. Alternatively or additionally, the communications are directed to allowing the analysis system 204 to control one or more aspects or features of the robot testing apparatus 202.

The robot testing apparatus 202 is configured to implement joint testing, such as rotational joint testing and translational joint testing of a joint. The robot testing apparatus 202 implements the rotational and translational joint testing to acquire or capture rotational and translational data indicative of rotational and translational movement of the joint during the rotational and translational joint testing, respectively. For instance, in implementing such testing, the robot testing apparatus 202 may be configured to detect a range of rotational motion and a range of translational motion for the joint. Other types of data indicative of rotational and translational movement of the joint during the rotational and translational joint testing may be acquired. For instance, the rotational and translational data acquired by the robot testing apparatus 202 may be indicative of a position (e.g., a relative position) of the joint for a given torque level.

Various types of rotational and translational joint testing may be implemented by the robot testing apparatus 202. In examples in which the joint is a knee, the rotational movement may be or include external-internal rotational movement and/or varus-valgus rotational movement. The translational movement may be or include anterior-posterior movement. Additional and/or alternative rotational and/or translational movements may be measured. The number of different rotational and translational joint tests implemented by the robot testing apparatus 202 may vary accordingly.

In some cases, the joint testing is cyclical joint testing. Each rotational or translational test may include a number of cycles of motion from one endpoint of the test to the other endpoint of the test. For example, a rotational test may involve movement from maximum internal rotation to maximum external rotation, or vice versa, for a given torque level. In one example, three and one-half cycles are implemented. The cycles may be extracted or determined by finding the most extreme positions in the peaks and valleys of the sensor (e.g., position) data for the test. While the cycles are designed to repetitively test a joint to measure the response to a range of loads (e.g., torque levels), the data from each respective cycle may be used or processed separately, as described further below.

The robot testing apparatus 202 includes a number of motors 206, one or more sensors 208 directed to capturing data for the rotational joint testing ("rotational sensors"), and one or more sensors 210 directed to capturing data for the translational joint testing ("translational sensors"). Each sensor 208, 210 is configured to capture data indicative of position as the rotational and translational joint testing is implemented. The motors 206, the rotational sensor(s) 208, and the translational sensor(s) 210 may be otherwise configured as described above in connection with FIGS. 1-9. Also as described above, each motor 206 may include a torque transducer or sensor to capture data indicative of the torque level applied to the joint during the rotational and translational joint testing.

The robotic testing apparatus 202 is configured to apply a range of forces (e.g., torque levels) to a joint under test. One or more of the sensors 208, 210 capture position data during the resulting joint movement. The position data is combined with data from the torque sensor(s) to form load-deformation data for the joint under test. The load-deformation data for the joint may include a set of force-position data points over the range of forces.

The analysis system 204 includes a processor 212 and a memory 214 for processing the load-deformation data captured by the robot testing apparatus 202. The processor 212 is coupled to, or otherwise in communication with, the robot testing apparatus 202. In this example, the analysis system 204 also includes a display 216 for providing a user interface for an operator of the analysis system 204. The user interface may be directed to controlling the robot testing apparatus 202 and/or the analysis system 204. The user interface may be alternatively or additionally directed to presenting the results of the processing.

The processor 212 is coupled to the memory 214 to access instructions and/or other data stored on the memory 214. In the example of FIG. 10, input instructions 218, curve function instructions 220, and analysis instructions 222 are stored on the memory 214. The instructions 218, 220, 222 may be stored as one or more modules or instruction sets, and may be integrated to any desired extent. The memory 214 may have additional data stored thereon, such as load-deformation data for the joint under test or other joint instances. The memory 214 may be or include any number of storage devices, memories, and/or other computer-readable media.

The processor 212 is configured through execution of the input instructions 218 to obtain the load-deformation data and/or other data captured via the robot testing apparatus 202. In some cases, the input instructions 218 cause the processor 212 to request the load-deformation data from the robot testing apparatus 202. In other cases, the data may be received (e.g., provided) without a request. For instance the input instructions 218 may cause the processor 212 to access the memory 214 to obtain the load-deformation data.

The load-deformation data may thus be obtained in additional and/or alternative ways. For instance, the processor 212 may be configured to obtain the underlying translational or rotational data from the robot testing apparatus 202 for the rotational or translational joint testing. In some cases, such data may be raw sensor data. The input instructions 218 (and/or other instructions) may then cause the processor 212 to process the raw data to develop rotational or translational data. The extent to which the sensor data provided to the processor 212 is processed before analysis may vary. The sensor data may be normalized to any desired extent.

The input instructions 218 may cause the processor 212 to obtain load-deformation data for various types of rotational and translational joint testing. In one knee-based example, the input instructions 218 configure the processor 212 to obtain load-deformation data indicative of external-internal rotational movement of the knee and load-deformation data indicative of varus-valgus rotational movement of the knee. Fewer, alternative, or additional rotational data may be obtained. For example, the load-deformation data obtained may be solely indicative of varus-valgus rotational movement. In the one knee-based example, the load-deformation data is indicative of anterior-posterior translational movement of the knee. Alternative or additional translational data may be obtained. For example, the load-deformation data may be indicative of movement along a different direction or axis than the direction or axis along which anterior-posterior movement occurs.

In some cases, the input instructions 218 cause the processor 212 to request the load-deformation or other rotational or translational data from the robot testing apparatus 202. In other cases, the data may be received (e.g., provided) without a request. For instance the input instructions 218 may cause the processor 212 to access the memory 214 to obtain the translational or rotational data. The load-deformation data may then be generated or formed via processing of the translational or rotational data and/or other raw data (e.g., raw sensor data) in accordance with the input instructions 218 or other instructions executed by the processor 212.

The processor 212 is configured through execution of the curve function generation instructions 220 to generate a load-deformation curve function for the load-deformation data for captured via the robot testing apparatus 202 for the joint under test. The load-deformation curve function defines a curve fitted to the load-deformation data. A variety of different curve fitting techniques or procedures may be used. For instance, any of the curve techniques used in connection with functional data analysis may be used. In some examples, regression modeling techniques, principal component analysis (PCA), or other techniques are used. In other cases, one or more quadratic curves are fitted to the load-deformation data. Other polynomial functions of varying order may alternatively be used.

Data indicative of the curve function may be stored in the memory 214 and/or other data store. In the example of FIG. 10, the curve function data is stored in a database 224. The curve function data may include a set of parameters, such as polynomial coefficient, PCA factor levels, or other factors generated by the fitting procedure.

The curve function generation instructions 220 may include instructions for defining or otherwise preparing the load-deformation data for fitting. For instance, portions of the load-deformation data are excluded from the fitting processing in some cases. For example, the load-deformation data in an area in which the joint is unloaded, or not sufficiently loaded, may be excluded. Exclusion of such unloaded data may avoid having the fitting procedure process data not deemed to be as accurate as other data (e.g., when the joint is under load). The load-deformation data may be split into subsets or groups for other reasons. In some cases, the subsets are associated with portions or sections of the resulting curve. B-spline or other fitting procedures may be used to generate a respective curve for each such portion or section. The curve defined by the function may thus include any number of continuous curves or curve segments or sections.

Preparation of the load-deformation data may additionally or alternatively involve addressing hysteresis in the load-deformation data. The hysteresis arises from those cases in which the joint testing is cyclical in nature. In some cases, the load-deformation data is split into two subsets or groups, one for each direction of the joint movement (e.g., increasing or decreasing external rotation). In such cases, two curve functions are generated. For example, the two curve functions may define two quadratic curves, one for each direction of the joint movement. In these and other cases, the load-deformation data is non-averaged and non-registered torque-position data.

The hysteresis may be addressed in other ways. For instance, in some cases, the load-deformation data is processed so that data from the two subsets can be combined. The processing may include adjustments to the load-deformation data so that each subset has data disposed at standard or otherwise common torque levels. The load-deformation data from the two subsets may then be averaged at every increment of torque. The adjustments may include various interpolation techniques, including, for instance, linear interpolation, polynomial interpolation, or b-spline interpolation, to generate a set of interpolated torque-position or other load-deformation data points for the joint. In still other cases, the curve function generation instructions 220 cause the processor 212 to generate a curve function that defines a hysteresis curve fitted to the respective load-deformation data.

In some examples, the curve fit to the load-deformation data may collapse the hysteresis seen during testing by segmental averaging at each point along the Y-axis of the load-deformation curve or along the X-axis of the load-deformation curve. In other words, in a load-deformation scenario, the joint is first loaded to its most posterior position with its maximum posterior load. From its most posterior position, an anterior load is applied at a specific strain rate reaching its peak anterior load at its most anterior position followed by a reversal of the load to a posteriorly directed load at the same strain rate reaching a maximum posterior load at its maximum posterior position. If the force is parceled into 10 segments, then the force at its most posterior position is the first point, the second point is $4/5$ths of that force, the third point is $3/5$ths of that force, the fourth point is $2/5$ths of that force, the fifth point is $1/5$th of that force, the sixth point is now $1/5$th of the maximum anterior force, the seventh point is $2/5$th of the maximum anterior force, the eighth point is $3/5$ of the maximum anterior force the 9th point is $4/5$th of the maximum anterior force and the 10th point is the full maximum anterior force. In one example, the force is parceled into 500 points and the maximum force allowed is 222 N when performing the Anterior/Posterior Drawer Test. At each point of force, there is a position of the tibia when the force is applied from the anterior to posterior direction and a second point when the force is applied from the posterior to anterior position. These two points can be averaged to produce load-deformation data, and ultimately a load-deformation curve, representing the average position of the tibia during the application of a force at a constant strain rate to a maximum torque or load in each direction. Challenges may arise during testing in cases in which the test load is sampled over time and position is sampled over time. When a load-deformation curve is developed, load and position are mapped as previously described. This does not produce a data series such that position is measured in equal load segments nor is load measured in equal position segments. Furthermore, there are more points taken at the endpoints of a load-deformation curve where change in position is slowed as torque or load seen by the tibia increases exponentially. It is this curve fitting technique to allow identification of position at each segment of load that allows for collapse of the hysteresis curve. Typically, the segments are approximated using a linear technique, but interpolation methods may be used to interpolate data to evenly distribute the load with respect to the position of the tibia. Other techniques can be implemented to describe only the fully loaded segments of the load-deformation curve. In other words, the fully loaded segments of a load-deformation curve are defined from 0 load to the maximum anterior load during anterior loading and from 0 load to the maximum posterior load during posterior loading. A third order polynomial can then be fit to these two curves such that it is representative of the load-deformation curve of the knee during testing. Other techniques may be used to collapse the hysteresis curve in order to simplify the load-deformation curve for further analysis.

Once the curve function is generated, one or more features of the curve defined by the curve function may be analyzed to assess the joint. For instance, the curve feature(s) may be compared with the curve features of other instances of the joint. The other joint instances may be normal or abnormal (e.g., injured). Finding the best match in features may then identify one or more biomechanical characteristics of the joint.

In the example of FIG. 10, the curve analysis instructions 222 cause the processor 212 to quantify a feature of the load-deformation curve. In some cases, the feature is a slope of the load-deformation curve. For instance, the slope at endpoints of the curve may be used to evaluate endpoint stiffness. Because the curves may be rounded at the endpoints, the term "at" is used herein to mean any point along a curve within 10-20% of the endpoint. Alternatively or additionally, the slope at the zero torque point along the curve may be quantified. A higher or steeper slope represents a less compliant or stiffer joint, whereas a lower slope represents a more compliant or looser joint.

A wide variety of other features may be additionally or alternatively quantified. For instance, the shape of the curve may be quantified in various ways. For instance, a quantitative representation of the roundness (or other shape parameter) may be a useful feature comparison. A particular curve shape may be associated with a respective type of injury or other abnormality. The association may depend on the presence or absence of other features, as addressed below in connection with the compilation of a profile for the joint under test. The width of the hysteresis established by the curves (or curve segments) or the single hysteresis curve may also be used. In some cases, the width is measured at the zero torque level. Yet another feature may be or involve the distance or extent to an endpoint of the curve.

In some cases, the quantified feature is a derivative of the curve other than or in addition to the slope of the curve. For example, the first and second derivatives of the curve may be found. These and other derivatives may be quantified at various points along the curve, such as at the endpoint(s), at zero torque, or at any other torque level.

The quantified feature may also be one of the defining parameters of the curve function. In PCA examples, the feature may be quantified by extracting one of the PCA factor levels. In other cases, various types of coefficients may also be extracted for analysis.

In other cases, the feature may be quantified through application of the curve function. For instance, the curve function may be used to generate position data points for given torque levels or other load-deformation data points. A set of load-deformation data points may thus be generated from the curve function at standard or other intervals to enable subsequent comparisons or other processing. One or more data points of the set of load-deformation data points may then be extracted as the quantified feature(s).

Once the feature(s) is/are quantified, the curve analysis instructions 222 cause the processor 212 to implement a comparison of the quantified feature(s) of the load-deformation curve with preset load-deformation data to identify a biomechanical characteristic of the joint. The preset load-deformation data may be associated with a plurality of joint instances. For instance, the preset load-deformation data may include respective curve function slope data for each joint instance of the plurality of joint instances. The preset load-deformation data for the joint instances may have been generated using the same testing apparatus (or type of testing apparatus) used to acquire the load-deformation data for the joint under test. In that way, the patient set-up and other factors underlying the data acquisition are consistent across the joint instances. In the example of FIG. 10, the preset load-deformation data is stored in the database 224. Other data storage devices may be alternatively or additionally be used.

In some cases, the analysis may include implementation of a pattern detection procedure. The pattern detection procedure may be directed to analyzing the quantified feature(s) and/or determining whether the shape of the curve shape matches a predetermined curve shape. The detected patterns may be indicative of healthy or injured joints.

The comparison implemented via the curve analysis instructions 222 may be or include a point-wise comparison of the dataset generated from the curve function. That dataset may then be compared with the preset datasets for the plurality of joint instances. The point-wise comparison may be or include paired or unpaired t-tests. Other types of point-wise comparisons may be used.

In some cases, the analysis involves multiple comparisons. For example, multiple curve features may be quantified. Non-curve features may also be compared or analyzed in conjunction with the curve feature(s). A profile for the joint under test may thus be compiled, the profile including both curve and non-curve features in some cases. The profile may then be compared against other profiles of abnormal and/or normal joints. The other profiles may be stored as preset data (e.g., preset profile data) in the database 224. The preset data may be updated as new profile data is gathered and analyzed. The new profile data may then be associated with a confirmed diagnosis or other assessment of the joint condition. Data indicative of the assessment may thus be added to the profile for the joint. The performance of the analysis system 204 may thus be improved over time via the integration of new profile data into the database 224.

The multiple comparisons may also include one or more comparisons of the underlying load-deformation data, e.g., the load-deformation data used to generate the curve function. For example, a scatterplot or other representation of the underlying load-deformation data for the joint under test may be compared with other, preset scatterplots or data representations for other joint instances. Point-wise comparisons of the underlying data may thus be implemented. The point-wise comparisons described herein are thus not limited to comparing data points generated from fitted curves or curve functions.

A variety of non-curve feature data may be included in the profiles. For example, the profile may include height, weight, and other data indicative of the subject. The computed joint play quantity may also be incorporated into the profile. Any data that may be helpful to identifying a joint abnormality may be incorporated. For example, the profile data may specify data indicative of the bones that define the joint under test, such as structural characteristics of the bones, the three-dimensional surfaces of the bones, and the contact points between the bones. Any of these or other parameters may be involved in the analysis (e.g., comparison with the profile data) of the profile of the joint under test implemented via the analysis instructions 222.

The curve analysis instructions 222 may then configure the processor 212 to assess the profile to identify an abnormality of the joint under test. The assessment may include comparing the profile with the profile data to find one or more matches or closest matches. A profile match may identify multiple abnormalities.

Various combinations of the profile, point-wise, and other comparisons may be used. In these ways, the load-deformation curve may support a variety of different curve function-based analyses, or functional data analyses, of the movement of the joint under test. Any number of features of the load-deformation curve may be extracted or otherwise quantified for comparison with the preset load-deformation data and/or other analysis. The comparison or other analysis may be directed to identifying one or more characteristics of the joint. Characteristic(s) of the joint under test may then be identified by matching the joint under test with other joints having similar load-deformation curve data.

The extent of the point-wise and other comparisons may vary. The systems and methods are not limited to curve data comparisons implemented over the entire curve or curve data set, or on a point-by-point basis. One or more portions or subsets of the curve data may be analyzed and useful for assessing the condition of the joint, regardless of which portions of the underlying load-deformation data are used for fitting. For instance, comparisons may focus on the curve features or other curve data at an endpoint of the curve. The endpoint curve data may provide a quantitative representation of the extent to which the joint under test has a soft or hard endpoint. For example, for a given test, the slope of the curve at or near the endpoint may be indicative of the status or condition of a particular ligament or other element of the joint under test.

The load-deformation data may not be averaged across cycles. Test data may be captured or otherwise obtained or available for multiple cycles of joint movement. Averaging such data would affect both the magnitude and shape of the curve defined by the curve function. The effect on the shape of the curve can be unintentional. For instance, small offsets between the data of different cycles may lead to a substantial change on the stiffness exhibited by the curve as a whole. Accordingly, in some cases, the load-deformation data is taken only from a single cycle in an effort to avoid distorting the curve shape. For example, the third cycle of a test session may be used. The patient may still be getting accustomed to the robot testing apparatus during the first two cycles. Implementing four or more cycles may increase the likelihood of patient discomfort, e.g., when multiple, different tests are implemented in each testing session.

The analysis system 204 and the robot testing apparatus 202 may be integrated with one another to any desired extent. In the example of FIG. 10, the robot testing apparatus 202 includes a processor 226 and a memory 228. The processor 226 and the memory 228 may be dedicated to supporting the data acquisition and communication functions of the robot testing apparatus 202. For instance, the processor 226 and the memory 228 may not be configured to implement the quantification and evaluation aspects of the system 200. In other cases, the processor 226 and the memory 228 are involved in the execution of the input instructions 218, the curve function generation instructions 220, and the curve analysis instructions 222. In still other cases, the robot testing apparatus 202 and the analysis system 204 share one or more processing and/or memory components.

Each processor 212, 226 may be or include any number or type of processing cores, processors, processing units (e.g., a central processing unit or graphical processing unit), or processing systems. Each processor 212, 226 may be a component in a variety of systems. For example, each processor 212, 226 may be part of a standard personal computer or a workstation. Each processor 212, 226 may be or include one or more general processors, digital signal processors, application specific integrated circuits, field programmable gate arrays, servers, networks, digital circuits, analog circuits, combinations thereof, or other now known or later developed devices for analyzing and processing data.

Each memory 214, 228 may be or include any number or type of computer-readable memories, media, or other devices on which data is stored. Each memory 214, 228 may be or include a main memory, a static memory, or a dynamic memory. Each memory 214, 228 may include, but may not be limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one case, each memory 214, 228 may include a cache or random access memory for a processor. Alternatively or additionally, each memory 214, 228 may be separate from the processor, such as a cache memory of a processor, the system memory, or other memory. Each memory 214, 228 may be or include an external storage device or database for storing data. Examples may include a hard drive, compact disc ("CD"), digital video disc ("DVD"), memory card, memory stick, floppy disc, universal serial bus ("USB") memory device, or any other device operative to store data. Each memory 212, 228 may be operable to store instructions executable by a processor. The functions, acts or tasks illustrated in the figures or described herein may be performed by the programmed processor executing the instructions stored in the memory 214, 228. The functions, acts or tasks may be independent of the particular type of instruction set, storage media, processor or processing strategy and may be performed by software, hardware, integrated circuits, firmware, micro-code and the like, operating alone or in combination. Likewise, processing strategies may include multiprocessing, multitasking, parallel processing and the like.

Figure 11:
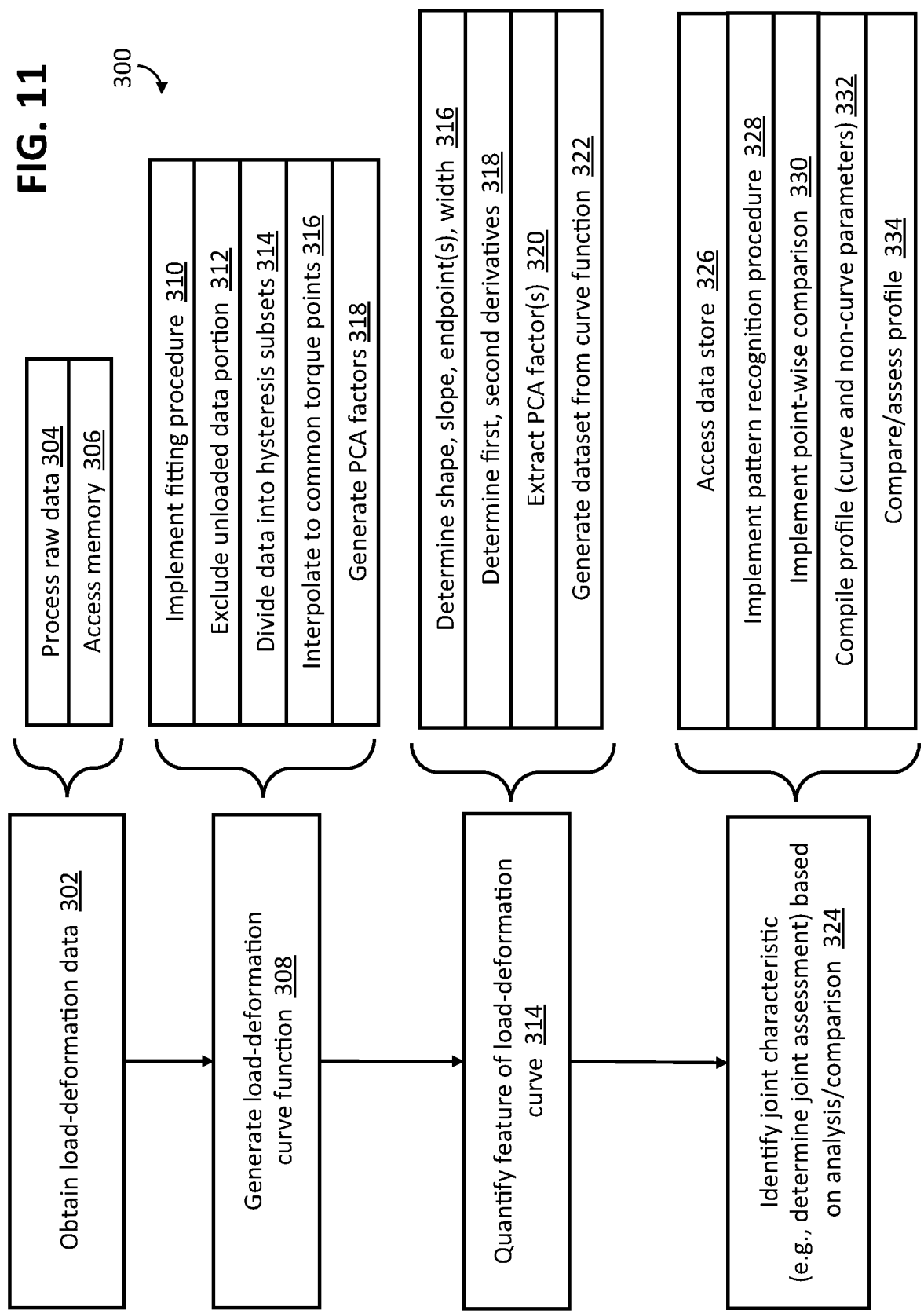
FIG. 11 is a flow diagram of a method for curve function-based biomechanical characterization and analysis of joints in accordance with one example.

FIG. 11 depicts a method 300 of biomechanical characterization and analysis of knees and other joints. The method 300 is computer-implemented. The method 300 may be implemented by the system 200 of FIG. 10. In some cases, for instance, the processor 212 (FIG. 10) implements one or more acts of the method 300. Alternatively or additionally, the processor 226 (FIG. 10) of the robot testing apparatus 202 implements one or more acts of the method 300. In these cases, the processor 212 and/or the processor 226 are configured via execution of computer-readable instructions, such as the instructions 218, 220, 222 (FIG. 10) stored in the memory 214 (FIG. 10), to cause the processor 212, 226 to implement the method 300. The method 300 may be implemented in additional and/or alternative ways. For instance, one or more acts of the method 300 may be implemented by a remote processor, such as a processor in communication with the processor 212 and/or the processor 226.

The method 300 includes an act 302 in which load-deformation data for a joint under test is obtained. The load-deformation data is representative of the response of the joint to applied forces (e.g., torques) in one or more rotational or translational tests. The joint testing is implemented by a robotic testing apparatus applied to the joint, such as the apparatus described above. The robotic test equipment may be configured to apply a range of forces to the joint and utilize sensors to gather the load-deformation data. Additional or alternative types of data may be acquired. For instance, the data may be indicative of a displacement for a given force or torque level. In cases in which the joint is a knee, the rotational movement may be or include varus-valgus rotational movement of the knee and/or external-internal rotational movement of the knee.

The manner in which the load-deformation data is obtained may vary. The act 302 may include the acquisition and/or processing of raw sensor data in an act 304. In other cases, the raw sensor data has already been processed and/or obtained, in which case the load-deformation data is obtained by accessing a memory in an act 306.

The method 300 includes an act 304 in which a load-deformation curve function is generated for the load-deformation data. As described above, the load-deformation curve function defines a curve fitted to the load-deformation data. In the example of FIG. 11, the act 304 includes an act 310 in which one or more fitting procedures are implemented. The fitting may be based on a subset of the load-deformation data as described above. For instance, an unloaded portion of the load-deformation data may be excluded from the subset in an act 312. Alternatively or additionally, the load-deformation data may be divided into hysteresis subsets in an act 314 in preparation for separate fittings. The data points in one or both hysteresis subsets may be adjusted, e.g., via interpolation, in an act 316 to provide common data points for averaging to address the hysteresis.

In some cases, the act 304 may include an act 318 in which the principal components of the load-deformation data are generated via principal component analysis (PCA) of the load-deformation data. Any number of principal components, or PCA factors, may be generated. One or more of the principle components of the load-deformation data may help identify various biomechanical characteristics of the joint under test. The overall health of joint, or particular injuries or ailments affecting the functioning of the joint may thus be identified.

A feature of the load-deformation curve function is quantified in an act 314. Quantifying the feature may include determining, in an act 316, a shape (e.g., a quantity representative of the shape) of the load-deformation curve, one or more slopes of the curve, one or more endpoints of the curve, and/or the width of the curve (e.g., at a zero torque level). When the quantified feature is the slope of the curve defined by the load-deformation curve, the slope may be determined at a zero torque level of the curve defined by the load-deformation curve function. In some cases the slope is determined at an endpoint of the curve defined by the load-deformation curve function. In other cases the slope is determined within the last twenty percent of data points before the endpoints of the load-deformation curve data are reached. A variety of other quantities may be determined, including, for instance, the first and second derivatives of the curve in an act 318. As described above, quantifying the feature may include determining or extracting one or more PCA factors in an act 320. Alternatively or additionally, quantifying the feature includes using the curve function to generate a set of data points for point-wise and/or other comparisons in an act 322. One or more of the data points may then be extracted as the quantified feature, as described above.

With the curve feature(s) quantified, a biomechanical characteristic of the joint is identified in an act 324 based on an analysis of the quantified feature of the joint. The biomechanical characteristic may be indicative of an injury or other abnormality of the joint. The analysis may be used to assess any condition or status of the joint. The act 324 may include accessing a data store, such as the database 224 (FIG. 10), to obtain preset data for comparison with the quantified feature(s) of the joint.

The act 324 may include detecting a pattern of the curve in an act 328. The biomechanical characteristic may be identified via implementation of a pattern recognition procedure. For instance, the procedure may determine whether the shape of the curve shape matches a predetermined curve shape presented via the preset data.

Alternatively or additionally, the act 324 may include implementing a point-wise comparison in an act 330. Data points generated in the act 322 may be compared with preset data points for one or more joint instances. Examples include a paired t-test and an unpaired t-test. Other comparisons may be used.

The joint characteristic identification of the act 324 may also or alternatively include compilation of a profile in an act 332. As described above, the profile may include non-curve parameters in addition to those quantified in the act 314. The profile may then be compared or otherwise assessed in an act 334. For instance, preset data indicative of the profiles of various abnormal joints (and/or normal joints) may be compared with the profile compiled for the joint under test.

The methods described herein may be implemented by software programs executable by a computer system. Further, implementations may include distributed processing, component/object distributed processing, and parallel processing. Alternatively or additionally, virtual computer system processing may be constructed to implement one or more of the methods or functionality as described herein.

As described above, the measured data from one or more single plane tests may be used to generate one or more load-deformation curves. The single-plane tests may be one of the above-described cyclical tests or other tests. A hysteresis curve may be generated for each test. A third-order polynomial or other curve may be generated using a fitting procedure that relies upon the loaded portions of the dataset. The curve may be used to interpolate or generate data for a standard set of torque points. The data need not be averaged across cycles or registered. The one or more load-deformation curves are used to characterize and assess the condition or status of the joint under test. One or more biomechanical characteristics of the joint may be identified via analysis of the load-deformation curves. Features may be extracted or otherwise quantified for each load deformation curve for comparative analysis. The analysis may include compiling a profile for the joint that includes both curve features and other information or data regarding the joint. Comparison of the profile with preset profile data for normal and/or abnormal joints may then determine the health, condition, or other status of the joint. Clinicians may thus be able to differentiate between joints where no differences would be seen using various manual, subjective techniques.

The computer-readable media referenced above may be a single medium or multiple media, such as a centralized or distributed database, and/or associated caches and servers that store one or more sets of instructions. The term "computer-readable medium" may also include any tangible medium that may be capable of storing, encoding or carrying a set of instructions for execution by a processor or that may cause a computer system to perform any one or more of the methods or operations disclosed herein. Such computer-readable media may be referred to as "computer-readable storage media."

The computer-readable medium may include a solid-state memory such as a memory card or other package that houses one or more non-volatile read-only memories. The computer-readable medium also may be a random access memory or other volatile re-writable memory. Additionally, the computer-readable medium may include a magneto-optical or optical medium, such as a disk or tapes or other storage device. A digital file attachment to an e-mail or other self-contained information archive or set of archives may be considered a distribution medium that may be a tangible storage medium. Accordingly, the disclosure may be considered to include any one or more of a computer-readable medium or a distribution medium and other equivalents and successor media, in which data or instructions may be stored.

Alternatively or additionally, dedicated hardware implementations, such as application specific integrated circuits, programmable logic arrays and other hardware devices, may be constructed to implement one or more of the methods described herein. Applications that may include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit. Accordingly, the present system may encompass software, firmware, and hardware implementations.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding only, and no unnecessary limitations should be understood therefrom, as modifications within the scope of the invention may be apparent to those having ordinary skill in the art.

What is claimed is:

1. A method of evaluating a joint of a patient, the method comprising:
    capturing load-deformation data by robotic testing equipment for the joint, the load-deformation data being gathered via joint testing implemented by the robotic test equipment, the robotic test equipment comprising a motor configured to drive movement of the joint and further comprising sensors to gather the load-deformation data during the movement;
    generating, by a processor, a load-deformation curve function for the load-deformation data, the load-deformation curve function defining a curve fitted to the load-deformation data;
    quantifying, by the processor, a feature of the curve defined by the load-deformation curve function; and
    identifying, by the processor, a biomechanical characteristic of the joint based on the quantified feature of the curve defined by the load-deformation curve function to assess a condition of the joint, wherein the quantified feature is indicative of a shape of the curve.

2. The method of claim 1, wherein identifying the biomechanical characteristic comprises detecting a pattern of the curve based on the quantified feature.

3. The method of claim 1, wherein identifying the biomechanical characteristic comprises implementing a pattern recognition procedure to determine whether the shape of the curve shape matches a predetermined curve shape.

4. The method of claim 1, further comprising:
    generating a set of load-deformation data points for the joint in accordance with the load-deformation curve function; and
    extracting a respective load-deformation data point of the set of load-deformation data points.

5. The method of claim 4, wherein identifying a biomechanical characteristic comprises implementing a point-wise comparison of the set of load-deformation data points with preset load-deformation data points disposed at torque levels in common with the set of load-deformation data points.

6. The method of claim 5, wherein the point-wise comparison comprises a paired t-test.

7. The method of claim 1, wherein:
    the load-deformation data exhibits hysteresis; and
    generating the load-deformation curve function comprises averaging the load-deformation data at common torque levels.

8. The method of claim 1, wherein generating the load-deformation curve function comprises:
    implementing a fitting procedure based on a subset of the load-deformation data; and
    excluding an unloaded portion of the load-deformation data from the subset of the load-deformation data.

9. The method of claim 1, wherein the load-deformation curve function is a third-order polynomial function.

10. A method of evaluating a joint of a patient, the method comprising:
    capturing load-deformation data by robotic testing equipment for the joint, the load-deformation data being gathered via joint testing implemented by the robotic test equipment, the robotic test equipment comprising a motor configured to drive movement of the joint and further comprising sensors to gather the load-deformation data during the movement;
    generating, by a processor, a load-deformation curve function for the load-deformation data, the load-deformation curve function defining a curve fitted to the load-deformation data;
    quantifying, by the processor, a feature of the curve defined by the load-deformation curve function; and
    identifying, by the processor, a biomechanical characteristic of the joint based on the quantified feature of the curve defined by the load-deformation curve function to assess a condition of the joint, wherein:
    the curve defined by the load-deformation curve function is a hysteresis curve; and the quantified feature is a width of the hysteresis curve at a zero torque level.

11. A method of evaluating a joint of a patient, the method comprising:
    capturing load-deformation data by robotic testing equipment for the joint, the load-deformation data being gathered via joint testing implemented by the robotic test equipment, the robotic test equipment comprising a motor configured to drive movement of the joint and further comprising sensors to gather the load-deformation data during the movement;
    generating, by a processor, a load-deformation curve function for the load-deformation data, the load-deformation curve function defining a curve fitted to the load-deformation data;
    quantifying, by the processor, a feature of the curve defined by the load-deformation curve function; and
    identifying, by the processor, a biomechanical characteristic of the joint based on the quantified feature of the curve defined by the load-deformation curve function to assess a condition of the joint,
    wherein the quantified feature is a slope of the curve defined by the load-deformation curve function.

12. The method of claim 11, wherein the slope is determined at a zero torque level of the curve defined by the load-deformation curve function.

13. The method of claim 11, wherein the slope is determined at an endpoint of the curve defined by the load-deformation curve function.

14. A method of evaluating a joint of a patient, the method comprising:
- capturing load-deformation data by robotic testing equipment for the joint, the load-deformation data being gathered via joint testing implemented by the robotic test equipment, the robotic test equipment comprising a motor configured to drive movement of the joint and further comprising sensors to gather the load-deformation data during the movement;
- generating, by a processor, a load-deformation curve function for the load-deformation data, the load-deformation curve function defining a curve fitted to the load-deformation data;
- quantifying, by the processor, a feature of the curve defined by the load-deformation curve function; and
- identifying, by the processor, a biomechanical characteristic of the joint based on the quantified feature of the curve defined by the load-deformation curve function to assess a condition of the joint,
- wherein generating the load-deformation curve function comprises generating principal components of the load-deformation data via principal component analysis of the load-deformation data.

15. The method of claim 14, wherein the quantified feature is representative of a level of one of the generated principal components.

16. The method of claim 1, wherein identifying the biomechanical characteristic comprises:
- compiling a profile for the joint, the profile comprising the quantified feature;
- accessing a data store in which preset profile data for abnormal joints is stored; and
- comparing the profile with the preset profile data to determine an assessment of the joint, the assessment comprising the biomechanical characteristic.

17. A method of evaluating a joint of a patient, the method comprising:
- capturing load-deformation data by robotic testing equipment for the joint, the load-deformation data being gathered via joint testing implemented by the robotic test equipment, the robotic test equipment comprising a motor configured to drive movement of the joint and further comprising sensors to gather the load-deformation data during the movement;
- generating, by a processor, a load-deformation curve function for the joint based on the load-deformation data;
- generating, by the processor, a set of load-deformation data points for the joint using the load-deformation curve function;
- implementing, by the processor, a comparison of the set of load-deformation data points with preset load-deformation curve function data; and
- providing, by the processor, an indication of a biomechanical characteristic of the joint based on the comparison to assess a condition of the joint.

18. The method of claim 17, wherein:
- the set of load-deformation data points and the preset load-deformation curve function data are disposed at a common set of torque levels; and
- the comparison comprises a point-wise comparison of the set of load-deformation data points with the preset load-deformation curve function data.

19. The method of claim 18, wherein the point-wise comparison comprises an unpaired t-test.

20. The method of claim 17, wherein generating the load-deformation curve function comprises:
- implementing a fitting procedure based on a subset of the load-deformation data; and
- excluding an unloaded portion of the load-deformation data from the subset of the load-deformation data.

21. A system of evaluating a joint of a patient, the system comprising:
- a robotic testing apparatus comprising a motor configured to drive movement of the joint and further comprising sensors to gather load-deformation data during the movement;
- a storage device in which preset load-deformation data for a plurality of joint instances is stored;
- a memory in which input instructions, curve function generation instructions, and curve function analysis instructions are stored; and
- a processor coupled to the storage device and the memory;
- wherein the processor is configured to implement the input instructions to obtain the load-deformation data captured by the robotic testing apparatus for the joint,
- wherein the processor is configured to implement the curve function generation instructions to generate a load-deformation curve function for the load-deformation data for the joint, the load-deformation curve function defining a curve fitted to the load-deformation data, and
- wherein the processor is configured to implement the curve analysis instructions to quantify a feature of the curve defined by the load-deformation curve function, and to implement a comparison of the quantified feature of the curve and the preset load-deformation data to identify a biomechanical characteristic of the joint to assess a condition of the joint,
- wherein the quantified feature is a slope of the curve defined by the load-deformation curve function.

22. The system of claim 21, wherein:
- the joint testing is cyclical such that the load-deformation data comprises a pair of hysteresis subsets;
- the processor is configured to implement the curve generation instructions to generate a set of load-deformation data points for the joint and average the pair of hysteresis subsets using the set of load-deformation data points.

23. The system of claim 21, wherein the preset load-deformation data comprises respective curve function slope data for each joint instance of the plurality of joint instances.

* * * * *